(12) United States Patent
Obrecht et al.

(10) Patent No.: US 10,730,911 B2
(45) Date of Patent: Aug. 4, 2020

(54) BACKBONE-CYCLIZED PEPTIDOMIMETICS WITH GLP-1R MODULATING ACTIVITY

(71) Applicants: POLYPHOR AG, Allschwil (CH); Universität Zürich, Zürich (CH)

(72) Inventors: Daniel Obrecht, Bättwil (CH); Christian Bisang, Basel (CH); Anatol Luther, Binzen (DE); Steffen Weinbrenner, Constance (DE); John Anthony Robinson, Wermatswil (CH); Kerstin Moehle, Wettswil (CH); Christian Steuer, Zürich (CH); William J. Drury, III, Gothenburg (SE)

(73) Assignees: UNIVERSITAT ZURICH, Zurich (CH); POLYPHOR AG, Allschwil (CH)

( * ) Notice: Subject to any disclaimer, the term of this patent is extended or adjusted under 35 U.S.C. 154(b) by 0 days.

(21) Appl. No.: 15/564,539

(22) PCT Filed: Apr. 6, 2016

(86) PCT No.: PCT/EP2016/025032
§ 371 (c)(1),
(2) Date: Oct. 5, 2017

(87) PCT Pub. No.: WO2016/162127
PCT Pub. Date: Oct. 13, 2016

(65) Prior Publication Data
US 2018/0072774 A1     Mar. 15, 2018

(30) Foreign Application Priority Data

Apr. 8, 2015  (EP) .................................. 15001000

(51) Int. Cl.
| | |
|---|---|
| *A61K 38/08* | (2019.01) |
| *A61K 38/12* | (2006.01) |
| *C07K 7/54* | (2006.01) |
| *C07K 7/64* | (2006.01) |
| *C07K 14/72* | (2006.01) |
| *A61K 38/02* | (2006.01) |
| *C07K 1/04* | (2006.01) |
| *C07K 14/00* | (2006.01) |
| *C07K 14/47* | (2006.01) |
| *C07K 14/655* | (2006.01) |
| *C07K 14/705* | (2006.01) |
| *C40B 50/14* | (2006.01) |
| *A61K 38/00* | (2006.01) |

(52) U.S. Cl.
CPC ............ *C07K 7/54* (2013.01); *A61K 38/02* (2013.01); *C07K 1/04* (2013.01); *C07K 7/64* (2013.01); *C07K 14/001* (2013.01); *C07K 14/4702* (2013.01); *C07K 14/6555* (2013.01); *C07K 14/705* (2013.01); *C07K 14/723* (2013.01); *C40B 50/14* (2013.01); *A61K 38/00* (2013.01)

(58) Field of Classification Search
CPC ...... A61K 38/08; C07K 7/06; C07K 14/6555; C07K 7/64
See application file for complete search history.

(56) References Cited

FOREIGN PATENT DOCUMENTS

| CN | 101 985 470 A | 3/2011 | |
|---|---|---|---|
| EP | 2 578 599 A1 | 4/2013 | |
| WO | WO 02/10192 A2 | 2/2002 | |
| WO | WO-2010015287 A2 * | 2/2010 | ............... C07K 7/56 |
| WO | WO 2010/127704 A1 | 11/2010 | |
| WO | WO 2012/016595 A1 | 2/2012 | |
| WO | WO 2015/013168 A1 | 1/2015 | |

OTHER PUBLICATIONS

CDC, Type 1 Diabetes, available online at: https://www.cdc.gov/diabetes/basics/type1.html, access on Jan. 3, 2020. (Year: 2020).*
Mayo Clinic, Obesity—Diagnosis and treatment, available online at: https://www.mayoclinic.org/diseases-conditions/obesity/diagnosis-treatment/drc-20375749, accessed on Jan. 3, 2020. (Year: 2020).*
Wilberger et al., Merck Manual, Traumatic Brain Injury (TBI), available online at: https://www.merckmanuals.com/professional/injuries-poisoning/traumatic-brain-injury-tbi/traumatic-brain-injury-tbi#, accessed on Jan. 6, 2020. (Year: 2020).*
Geji et al., Front. Aging Neurosci., 2016, 8:108. (Year: 2016).*

(Continued)

*Primary Examiner* — James H Alstrum-Acevedo
*Assistant Examiner* — Kaipeen E Yang
(74) *Attorney, Agent, or Firm* — Medler Ferro Woodhouse & Mills PLLC

(57) ABSTRACT

Novel backbone-cyclized peptidomimetics of the general formula

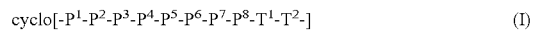

cyclo[-$P^1$-$P^2$-$P^3$-$P^4$-$P^5$-$P^6$-$P^7$-$P^8$-$T^1$-$T^2$-]   (I)

wherein the single elements T or P are α-amino acid residues connected in either direction which, depending on their positions in the chain, are as defined in the description and the claims, and salts thereof, have the property to modulate the GLP-1 receptor. They can be used as medicaments to treat, prevent, or delay the onset of diseases, disorders or conditions in which modulation of the human GLP-1 receptor is beneficial, such as type 2 diabetes.

These backbone-cyclized peptidomimetics can be manufactured by a process which is based on a mixed solid—and solution phase synthetic strategy.

15 Claims, No Drawings

(56) References Cited

OTHER PUBLICATIONS

By Healthline, Crohn's Disease: Causes, Symptoms, Diagnosis, and More, available online at: https://www.healthline.com/health/crohns-disease, accessed on 2020. (Year: 2020).*

Alzheimer's Disease Fact Sheet (NIH, National Institute on Aging, available online at: https://www.nia.nih.gov/health/alzheimers-disease-fact-sheet, accessed on Jan. 6, 2020. (Year: 2020).*

Hammond (Multiple Sclerosis Prevention: Is It Possible? https://www.healthline.com/health/multiple-sclerosis-prevention, accessed on 2020. (Year: 2020).*

International Search Report for PCT/EP2016/025032, dated Jul. 1, 2016.

Fasan et al., "Structure-Activity Studies in a Family of beta-Hairpin Protein Epitope Mimetic Inhibitors of the p53-HDM2 Protein-Protein Interaction," *ChemBioChem* 7(3):515-526 (2006).

Mapelli et al., "Eleven Amino Acid Glucagon-like Peptide-1 Receptor Agonists with Antidiabetic Activity," *Journal of Medicinal Chemistry* 52(23):7788-7799 (2009).

Schmidt et al., "Structural studies of β-hairpin peptidomimetic antibiotics that target LptD in *Pseudomonas* sp.," *Bioorganic & Medicinal Chemistry* 21(18):5806-5810 (2013).

Hoang et al., "Short Hydrophobic Peptides with Cyclic Constraints Are Potent Glucagon-like Peptide-1 Receptor (GLP-1R) Agonists," *Journal of Medicinal Chemistry* 58(9):4080-4085 (2015).

* cited by examiner

BACKBONE-CYCLIZED PEPTIDOMIMETICS WITH GLP-1R MODULATING ACTIVITY

The present invention provides backbone-cyclized peptidomimetics of formula (I),

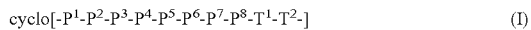
$$\text{cyclo}[-P^1-P^2-P^3-P^4-P^5-P^6-P^7-P^8-T^1-T^2-] \quad (I)$$

comprising a chain of 8 α-amino acid residues $P^1$ to $P^8$ attached to a template $T^1$ and $T^2$, as defined herein below.

These backbone-cyclized peptidomimetics are able to modulate the biological function of glucagon-like peptide-1 receptor, abbreviated GLP-1R, and may thus be useful as pharmaceuticals in the treatment or prevention of a variety of diseases, conditions and disorders, in particular, in the treatment of type 2 diabetes. In addition, the present invention also relates to pharmaceutical compositions and forms comprising one or more of these compounds and efficient processes for the preparation and production of these compounds.

Many medical relevant biological processes are mediated by signal transduction that involves G protein-coupled receptors (GPCRs) and their endo- or exogenic ligands. Among the diverse members of the GPCR superfamily the class B1 GPCRs comprise the secretin-like receptors, including GLP-1R (A. Couvineau and M. Laburthe, *Curr. Drug Targets* 2012, 13, 103-115). The regulatory system based on the interaction between GLP-1R and its cognate ligand glucagon-like peptide-1 (GLP-1) is involved in diverse metabolic and non-metabolic effects. GLP-1, a member of the incretin hormones, is secreted from enteroendocrine L-cells in response to food intake (e.g. J. E. Campbell and D. J. Drucker, *Cell. Metab.* 2013, 17, 819-837) and its glycaemic actions have been studied in detail. These include glucose-dependent insulin secretion from pancreatic β-cells by GLP-1, suppression of glucagon secretion, slowing of gastric emptying, and appetite suppression (e.g. L. L. Baggio and D. J. Drucker, *Gastroenterology* 2007, 132, 2131-2157; M. A. Nauck, *Am. J. Med.* 2009, 122, S3-S10). Apart from glycaemic effects mediated via GLP-1R agonists, non-glycaemic effects have been identified and are intensively pursued for exploitation in therapeutic use (T. Vilsboll and A. J. Garber, *Diabetes Obes. Metab.* 2012, 14 [Suppl. 2], 41-49 and literature cited therein). Beneficial effects of GLP-1 in lowering glucose levels in humans have been reported in the early 1990s (D. M. Nathan et al., *Diabetes Care* 1992, 15, 270-276). However, a very short half-life has been observed for native GLP-1 (7-36) amide (T. Vilsboll et al., *J. Clin. Endocrinol. Metab.* 2003, 88, 220-224). Therefore, different strategies have been applied for the development of drugs based on the incretin hormone GLP-1, aiming, for example, at improved plasma stability (e.g. J. J. Meier, *Nat. Rev. Endocrinol.* 2012, 8, 728-742 and literature cited therein; L. P. Miranda et al., *J. Med. Chem.* 2008, 51, 2758-2765). An alternative approach is based on GLP-1 mimetics, including exendin-4, a 39 amino acids peptide that was identified from the Glia monster lizard (J. Eng et al., *J. Biol. Chem.* 1992, 267, 7402-7405).

Both approaches have led to marketed drugs for the treatment of type 2 diabetes (e.g. A. Lund et al., *Eur. J. Intern. Med.* 2014, 25, 407-414; Y. M. Cho et al., *Endocrinol. Metab. (Seoul)* 2013, 28, 262-274; A. J. Garber, *Diabetes Care* 2011, 34 [Suppl. 2], S279-S284).

Studies on the interaction between GLP-1R and GLP-1 or truncated or mutated versions thereof were useful to support the discovery of smaller peptidic GLP-1 mimetics and analogues (e.g. C. R. Underwood et al., *J. Biol. Chem.* 2010, 285, 723-730). These include, for example, linear 11-mer peptide GLP-1 mimetics that were pursued in preclinical development (C. Mapelli et al., *J. Med. Chem.* 2009, 52, 7788-7799).

Identification of suitable, small molecule GLP-1R modulators has proven to be difficult and is less advanced (F. S. Willard et al., *Exp. Diabetes. Res.* 2012, 2012:709893), examples including TTP-054 (WO2011/031620 A1), Boc5 (D. Chen et al., *Proc. Natl. Acad. Sci. U.S.A.* 2007, 104, 943-948), BETP (K. W. Sloop et al., *Diabetes* 2010, 59, 3099-3107), and "Compound 2" (L. B. Knudsen et al., *Proc. Natl. Acad. Sci. U.S.A.* 2007, 104, 937-942; N. Irwin et al., *Eur. J. Pharmacol.* 2010, 628, 268-273; K. Coopman et al., *J. Pharmacol. Exp. Ther.* 2010, 334, 795-808).

Additionally, signaling biases at the GLP-1R were studied for various GLP-1R modulators (e.g. D. Wootten et al., *Mol. Pharmacol.* 2013, 83, 822-834), and coupling of the GLP-1R to different pathways was suggested to be associated with distinct therapeutic and side-effect profiles (e.g. K. Pabreja et al., *Br. J. Pharmacol.* 2014, 171, 1114-1128 and literature cited therein).

In addition to the use for treatment of type 2 diabetes, GLP-1R agonists are emerging with further promising therapeutic uses in the treatment of diseases such as type 1 diabetes (e.g. U. Kielgast et al., *Curr. Diabetes Rev.* 2009, 5, 266-275; U. Kielgast et al., *Diabetes* 2011 60, 1599-1607) and in the treatment of prediabetes (H. Ahmadieh and S. T. Azar, *Prim. Care Diabetes*, DOI: 10.1016/j.pcd.2014.02.005; J. J. Hoist and C. F. Deacon, *Trends Endocrinol. Metab.* 2013, 145-152; S. Cernea, Rev. Diabet. Stud., 2011, 8, 223-238; S. Cernea and I. Raz, *Diabetes Care* 2011, 34 [Suppl. 2], S264-S271 and literature cited therein) such as impaired glucose tolerance.

GLP-1R agonists have further been reported for other emerging therapeutic uses in the treatment of diabetes-related complications as well as of diabetes-related comorbidities (Y. Seino and D. Yabe, *J. Diabetes Investig.* 2013, 4, 108-130 and literature cited therein), including diseases such as diabetic retinopathy (L. Varadhan et al., *Diabetes Res. Clin. Pract.* 2014, 103, e37-e39; A. Puddu et al., *Mediators. Inflamm.* 2013, 2013: 975032); diabetic neuropathy (M. Kan et al., *J. Neuropathol. Exp. Neurol.* 2012, 71, 494-510); diabetic nephropathy (M. H. Muskiet, *Nat. Rev. Nephrol.* 2014, 10, 88-103); dyslipidemia (E. A. Schwartz et al., *Atherosclerosis* 2010, 212, 217-222; J. J. Meier et al., *Diabetologia* 2006, 49, 452-458); vascular diseases (S. Yamagishi and T. Matsui, *Curr. Pharm. Des.* 2011, 17, 4379-4385; D. Lorber, *Cardiovasc. Ther.* 2013, 31, 238-249 and literature cited therein); and obesity (A. J. Scheen and L. F. Van Gaal, *Lancet Diabetes Endocrinol.*, DOI: 10.1016/S2213-8587(14)70004-X; A. Ottney, *Am. J. Health Syst. Pharm.* 2013, 70, 2097-2103; R. C. Troke et al., *Ther. Adv. Chronic Dis.* 2014 51, 4-14).

The use of GLP-1R agonists has recently also been investigated for the potential treatment of cognitive deficits (e.g. R. S. McIntyre et al., *Behav. Brain Res.* 2013, 237, 164-171 and literature cited therein); treatment of mood disorders (R. Isacson et al., *Eur. J. Pharmacol.* 2011, 650, 249-255); treatment of neurodegenerative diseases (C. Holscher, *J. Endocrinol.* 2014, 221, T31-T41 and literature cited therein), including diseases such as Alzheimer's disease (P. L. McClean and C. Holscher, *Neuropharmacology* 2014, 76 Pt A: 57-67; K. Talbot and H. Y. Wang, *Alzheimers Dement.* 2014, 10, S12-S25); treatment of traumatic brain injuries (N. H. Greig et al., *Alzheimers Dement.* 2014, 10, S62-S75 and literature cited therein); treatment of stroke (V. Darsalia et al., *Rev. Endocr. Metab. Disord.* 2014, 15, 233-234); treatment of insufficient satiety (K. P. Skibicka, *Front. Neurosci.* 2013, 7:181; A. Flint et al., *J. Clin. Invest.* 1998, 101, 515-520; B. L. van Bloemendaal et al., *J. Endocrinol.* 2014, 221, T1-16); treatment of cardiovascular diseases (M. Lehrke and N. Marx, *Rev. Diabet. Stud.* 2011, 8, 382-391; J. R. Ussher and D. J. Drucker, *Circ. Res.* 2014, 114, 1788-1803; J. R. Ussher and D. J. Drucker, *Endocr. Rev.* 2012, 33, 187-215), including diseases such as myocardial infarction (N. Mikhail, *Endocrine* 2014, 47, 21-28; S. Ravassa et al., *Endocrinol. Nutr.* 2012, 59, 561-569); treatment of artherosclerosis (Y. Wang et al., *Br. J. Pharmacol.* 2014, 171, 723-734; Y. Tashiro et al., *Peptides* 2014, 54, 19-26 and literature cited therein); treatment of gastric ulcers (A. Wettergren et al., *Dig. Dis. Sci.* 1993, 38, 665-673; A. Wettergren et al., *Gut* 1997, 40, 597-601); treatment of inflammatory bowel syndrome (D. Kunkel et al., *Neurogastroenterol. Motil.* 2011, 23, 739-e328); and treatment of obesity (J. L. Estall and D. J. Drucker, *Curr. Pharm. Des.* 2006, 12, 1731-1750; R. C. Troke et al., *Ther. Adv. Chronic. Dis.* 2014, 5, 4-14; A. S. Kelly et al., *JAMA Pediatr.* 2013, 167, 355-360).

Furthermore, GLP-1R agonists have been evaluated in clinical trials for use in treatment of hyperglycemia (J. Gerich, *Int. J. Gen. Med.* 2013, 6, 877-895; M. M. Byrne et al., *Diabetes* 1998, 47, 1259-1265); treatment of metabolic syndrome (M. Tesauro et al., *Diabetes Care* 2013, 36, 683-689); hypertension (J. P. Gutzwiller et al., *J. Clin. Endocrinol. Metab.* 2004, 89, 3055-3061); and insulin resistance (P. Grigoropoulou et al., *Curr. Diabetes Rev.* 2013, 9, 412-417).

The present invention provides new chemical entities for a potential use as druggable modulators of GLP-1R. In the compounds described below, a loop sequence with elements $P^1$ to $P^8$ is grafted onto a template consisting of elements $T^1$ and $T^2$.

The backbone-cyclized peptidomimetics of this invention thus comprise cyclic 10-mer peptides which are significantly shorter than the cognate ligand GLP-1 with a length of 30 amino acids and the GLP-1 mimetic Exendin-4 with a length of 39 amino acids. In addition, through their cyclic nature they differ from similar-sized, linear 11-mer peptide GLP-1 mimetics mentioned above.

Template-bound hairpin mimetic peptides have been described in the literature (D, Obrecht, M. Altorfer, J. A. Robinson, *Adv. Med. Chem.* 1999, 4, 1-68; J. A. Robinson, *Syn. Lett.* 2000, 4, 429-441) and the ability to generate cyclic β-hairpin peptido-mimetics using combinatorial and parallel synthesis methods has been established (L. Jiang, K. Moehle, B. Dhanapal, D. Obrecht, J. A. Robinson, *Helv. Chim. Acta.* 2000, 83, 3097-3112). These methods allow the synthesis and screening of large β-hairpin mimetic libraries, which in turn considerably facilitates structure-activity studies and hence the discovery of new molecules.

The invention relates to novel backbone-cyclized peptidomimetics of formula (I),

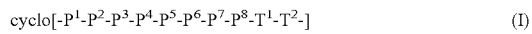 (I)

wherein the single elements T or P are connected in either direction from the carbonyl (C=O) point of attachment to the nitrogen (N) of the next element and wherein $T^1$ is a D α-amino acid residue of formula

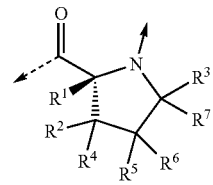 AA1

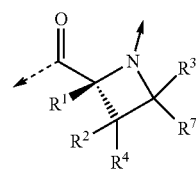 AA2

$T^2$ is an L or D α-amino acid residue of one of the formulae

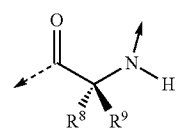 AA3

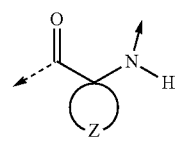 AA4

$P^1$ is Phe; Tyr; 3Pal; 2Thi; or 3Thi;
$P^2$ is Asp; Asn; Glu; Hgl; Gln; hGln; Cit; or an L α-amino acid residue of formula

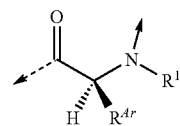 AA5

$P^3$ is Leu; Nle; Cha; Chg; Asn; Gln; hGln; or Cit;
$P^4$ is Leu; Nle; Val; or an L α-amino acid residue of formula

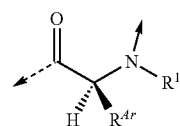 AA5

$P^5$ is Ala; Aib; or Abu;
$P^6$ is Trp; Trp(5OH); Tpi; or Trp(1Me);
$P^7$ is Asp; Asn; Glu; Hgl; Gln; hGln; or Cit;
$P^8$ is Arg; hArg; Agp; Lys; hLys; Orn; or an L α-amino acid residue of formula

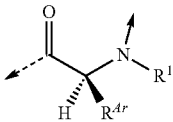

AA5 with the proviso that
if P³ is Asn; Gln; hGln; or Cit; then
  P² is an L α-amino acid residue of formula AA5;
  P⁷ is Asp; Glu; Hgl; or Cit;
or if P³ is Leu; Nle; Cha; or Chg; and P² is Asn; Gln; hGln; Cit; or an L α-amino acid residue of formula AA5; then
  P⁷ is Glu; or Hgl;
$R^{Ar}$ is, with the proviso of containing less than 26 carbon- and/or heteroatoms, $-(CR^{20}R^{22})_n R^{27}$; $-(CH_2)_n O(CH_2)_m R^{27}$; $-(CH_2)_n S(CH_2)_m R^{27}$; or $-(CH_2)_n NR^{25}(CH_2)_m R^{27}$;
$R^1$, $R^2$ and $R^3$ are independently
  H; $CF_3$; or $CH_3$;
$R^4$, $R^5$ and $R^6$ are independently
  H; F; $CF_3$; $C_{1-8}$-alkyl; $C_{2-8}$-alkenyl; $C_{2-8}$-alkynyl; cycloalkyl; heterocycloalkyl; $-(CHR^{12})_o OR^{15}$; $-O(CO)R^{15}$; $-(CHR^{12})_o SR^{15}$; $-(CHR^{12})_o NR^{15}R^{16}$; $-(CHR^{12})_o OCONR^{15}R^{16}$; $-(CHR^{12})_o NR^1 CONR^{15}R^{16}$; $-(CHR^{12})_o NR^1 COOR^{15}$; $-(CHR^{12})_o NR^1 COR^{15}$; $-(CHR^{12})_o COOR^{15}$; $-(CHR^{12})_o CONR^{15}R^{16}$; $-(CHR^{12})_o PO(OR^1)_2$; $-(CHR^{12})_o SO_2 R^{15}$; $-(CHR^{12})_o NR^1 SO_2 R^{15}$; or $-(CHR^{12})_o SO_2 NR^{15}R^{16}$;
$R^4$ and $R^2$; or $R^5$ and $R^6$ taken together can form:
  =O; or $-(CHR^1)_p-$;
$R^4$ and $R^5$; or $R^6$ and $R^7$ taken together can form:
  $-(CHR^1)_p-$; $-(CH_2)_t O(CH_2)_u-$; $-(CH_2)_t S(CH_2)_u-$; or $-(CH_2)_t NR^1 (CH_2)_u-$;
$R^7$ is H; F; $CF_3$; $C_{1-8}$-alkyl; $C_{2-8}$-alkenyl; $C_{2-8}$-alkynyl; cycloalkyl; heterocycloalkyl; $-(CHR^{12})_r OR^{15}$; $-O(CO)R^{15}$; $-(CHR^{12})_r SR^{15}$; $-(CHR^{10})_r NR^{15}R^{16}$; $-(CHR^{12})_r OCONR^{15}R^{16}$; $-(CHR^{12})_r NR^1 CONR^{15}R^{16}$; $-(CHR^{12})_r NR^1 COOR^{15}$; $-(CHR^{12})_r NR^1 COR^{15}$; $-(CHR^{12})_o COOR^{15}$; $-(CHR^{12})_o CONR^{15}R^{16}$; $-(CHR^{12})_o PO(OR^1)_2$; $-(CHR^{12})_r SO_2 R^{15}$; $-(CHR^{12})_r NR^1 SO_2 R^{15}$; or $-(CHR^{12})_r SO_2 NR^{15}R^{16}$;
$R^8$ and $R^9$ are, with the proviso of containing combined less than 26 carbon- and/or heteroatoms, independently $C_{1-8}$-alkyl; $C_{2-8}$-alkenyl; $C_{2-8}$-alkynyl; cycloalkyl-$C_{1-4}$-alkyl; heterocycloalkyl-$C_{1-4}$-alkyl; $-(CHR^1)_s OCF_3$; $-(CHR^1)_s OR^{18}$; $-(CHR^1)_s SCF_3$; or $-(CHR^1)_s SR^{18}$;
Z is, with the proviso of containing less than 26 carbon- and/or heteroatoms, $-(CR^2 R^{12})_q-$; $-(CR^2 R^{12})_k O(CR^2 R^{12})_l-$; or $-(CR^2 R^{12})_k S(CR^2 R^{12})_l-$;
or a group of one of the formulae

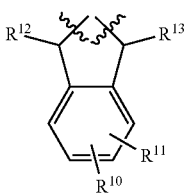

Z1

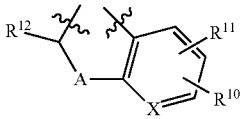

Z2

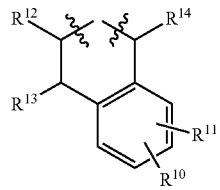

Z3

A is O; $NR^{17}$; S; SO; or $SO_2$;
X is $-CR^{19}$; or N;
$R^{10}$ and $R^{11}$ are independently
  H; F; Cl; Br; I; $CF_3$; $OCF_3$; $OCHF_2$; $C_{1-4}$-alkyl; $C_{2-4}$-alkenyl; or $C_{2-4}$-alkynyl;
$R^{12}$, $R^{13}$ and $R^{14}$ are independently
  H; F; $CF_3$; or $CH_3$;
$R^{15}$ and $R^{16}$ are independently
  H; $C_{1-8}$-alkyl; $C_{2-8}$-alkenyl; $C_{2-8}$-alkynyl; $C_{1-6}$-alkoxy; cycloalkyl; heterocycloalkyl; cycloalkyl-$C_{1-6}$-alkyl; or heterocycloalkyl-$C_{1-6}$-alkyl; or
the structural element $-NR^{15}R^{16}$ can form heterocycloalkyl;
$R^{17}$ is H; $C_{1-4}$-alkyl; $C_{2-4}$-alkenyl; or $C_{2-4}$-alkynyl;
$R^{18}$ is $C_{1-4}$-alkyl; $C_{2-4}$-alkenyl; or $C_{2-4}$-alkynyl;
$R^{19}$ is H; F; Cl; Br; I; CN; $CF_3$; $OCHF_2$; $OCF_3$; $C_{1-4}$-alkyl; $C_{2-4}$-alkenyl; or $C_{2-4}$ alkynyl;
$R^{20}$ and $R^{21}$ are independently
  H; $CF_3$; $C_{1-8}$-alkyl; $C_{2-8}$-alkenyl; $C_{2-8}$-alkynyl; or aryl-$C_{1-6}$-alkyl;
$R^{22}$ is H; F; $CF_3$; $C_{1-8}$-alkyl; $C_{2-8}$-alkenyl; $C_{2-8}$-alkynyl; cycloalkyl; heterocycloalkyl; aryl; heteroaryl; aryl-$C_{1-6}$-alkyl; heteroaryl-$C_{1-6}$-alkyl; $-(CHR^{23})_o OR^{25}$; $-O(CO)R^{25}$; $-(CHR^{23})_o SR^{25}$; $-(CHR^{23})_o NR^{25}R^{26}$; $-(CHR^{23})_o OCONR^{25}R^{26}$; $-(CHR^{23})_o NR^{20} CONR^{25}R^{26}$; $-(CHR^{23})_o NR^{20} COOR^{25}$; $-(CHR^{23})_o NR^{20} COR^{25}$; $-(CHR^{23})_o COOR^{25}$; $-(CHR^{23})_o CONR^{25}R^{26}$; $-(CHR^{23})_o PO(OR^{20})_2$; $-(CHR^{23})_o SO_2 R^{25}$; $-(CHR^{23})_o NR^{20} SO_2 R^{25}$; $-(CHR^{23})_o SO_2 NR^{25}R^{26}$; $-(CR^{20}R^{23})_o R^{27}$; or $-(CHR^{20})_n O(CHR^{21})_m R^{27}$;
$R^{23}$ is H; F; $CF_3$; $C_{1-8}$-alkyl; $C_{2-8}$-alkenyl; $C_{2-8}$-alkynyl; cycloalkyl; heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; $-(CHR^{20})_o OR^{25}$; $-OCOR^{20}$; $-(CHR^{20})_o NR^{25}R^{26}$; $-COOR^{25}$; $-CONR^{25}R^{26}$; $-SO_2 R^{25}$; or $-SO_2 NR^{25}R^{26}$;
$R^{24}$ is H; $CF_3$; $C_{1-8}$-alkyl; $C_{2-8}$-alkenyl; $C_{2-8}$-alkynyl; cycloalkyl; heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; $-(CHR^{20})_o OR^{25}$; $-(CHR^{20})_o SR^{25}$; $-(CHR^{20})_o NR^{25}R^{26}$; $-(CHR^{20})_o COOR^{25}$; $-(CHR^{20})_o CONR^{25}R^{26}$; or $-(CHR^{20})_o SO_2 R^{25}$;
$R^{25}$ and $R^{26}$ are independently
  H; $C_{1-8}$-alkyl; $C_{2-8}$-alkenyl; $C_{2-8}$-alkynyl; $C_{1-6}$-alkoxy; cycloalkyl; heterocycloalkyl;
  cycloalkyl-$C_{1-6}$-alkyl; heterocycloalkyl-$C_{1-6}$-alkyl; aryl; heteroaryl;
  aryl-$C_{1-6}$-alkyl; heteroaryl-$C_{1-6}$-alkyl; cycloalkyl-aryl; heterocycloalkyl-aryl;
  cycloalkyl-heteroaryl; heterocycloalkyl-heteroaryl; aryl-cycloalkyl;

aryl-heterocycloalkyl; heteroaryl-cycloalkyl; or heteroaryl-heterocycloalkyl; or the structural element —NR$^{25}$R$^{26}$ can independently form:

heterocycloalkyl; aryl-heterocycloalkyl; or heteroaryl-heterocycloalkyl;

R$^{27}$ is an aryl group of one of the formulae

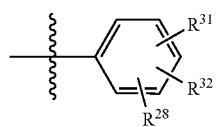
AR1

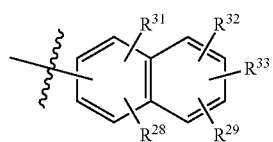
AR2 or a heteroaryl group of one of the formulae

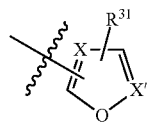
H1

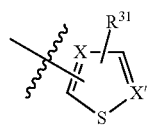
H2

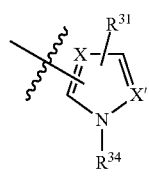
H3

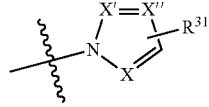
H4

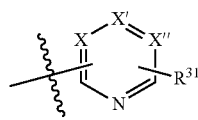
H5

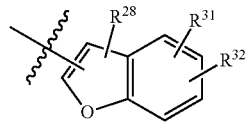
H6

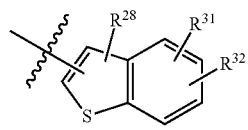
H7

-continued

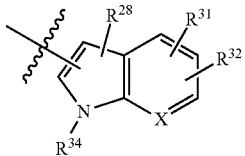
H8

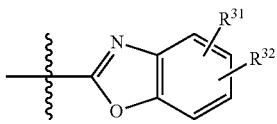
H9

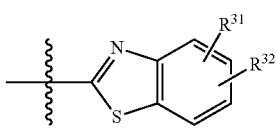
H10

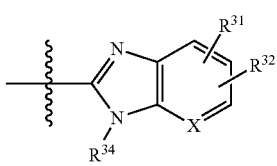
H11

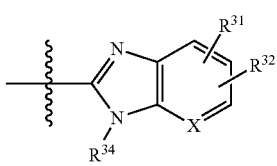
H12

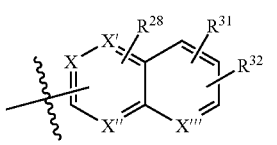
H13

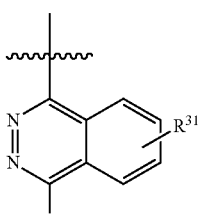
H14

X, X', X" and X'" are independently
—CR$^{28}$; or N;

R$^{28}$ and R$^{29}$ are independently

H; F; Cl; Br; I; OH; NH$_2$; NO$_2$; CN; CF$_3$; OCHF$_2$; OCF$_3$; C$_{1-8}$-alkyl; C$_{2-8}$-alkenyl;

C$_{2-8}$-alkynyl; aryl; heteroaryl; aryl-C$_{1-6}$-alkyl; heteroaryl-C$_{1-6}$-alkyl; —(CH$_2$)$_o$R$^{30}$;

—(CH$_2$)$_o$OR$^{25}$; —O(CO)R$^{25}$; —O(CH$_2$)$_o$R$^{30}$; —(CH$_2$)$_o$SR$^{25}$; —(CH$_2$)$_o$NR$^{25}$R$^{26}$;

—(CH$_2$)$_o$OCONR$^{25}$R$^{26}$; —(CH$_2$)$_o$NR$^{20}$CONR$^{25}$R$^{26}$; —(CH$_2$)$_o$NR$^{20}$COR$^{25}$; —(CH$_2$)$_o$COOR$^{25}$;

—(CH$_2$)$_o$CONR$^{25}$R$^{26}$; —(CH$_2$)$_o$PO(OR$^{20}$)$_2$; —(CH$_2$)$_o$SO$_2$R$^{24}$; or —(CH$_2$)$_o$COR$^{25}$;

$R^{30}$ is an aryl group of the formula

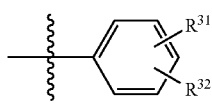

AR3

$R^{31}$, $R^{32}$ and $R^{33}$ are independently
H; F; Cl; Br; I; OH; $NH_2$; $NO_2$; CN; $CF_3$; $OCHF_2$; $OCF_3$;
$C_{1-8}$-alkyl; $C_{2-8}$-alkenyl; $C_{2-8}$-alkynyl;
—$(CH_2)_oR^{25}$; —$O(CO)R^{25}$; —$(CH_2)_oNR^{20}R^{25}$;
—$(CH_2)_o$ $COOR^{25}$; or —$(CH_2)_oCONR^{20}R^{25}$;

$R^{34}$ is H; Ac; $C_{1-8}$-alkyl; or aryl-$C_{1-6}$-alkyl;

k and l are independently an integer of 1-5 with the proviso that k+l≤6;

t and u are independently an integer of 0-3 with the proviso that t+u≥1 and t+u≤3;

n and m are independently an integer of 0-5 with the proviso that n+m≤6;

o is 0-4; p is 2-4; q is 3-7; r is 1-3; s is 1-4;

or a pharmaceutically acceptable salt thereof.

Each single group "$R^x$" with the same index-number x for x=1-34 is independently selected on each occurrence in a specific formula and, therefore, they can be the same or different.

As used in this description, the term "alkyl", taken alone or in combinations (i.e. as part of another group, such as "aryl-$C_{1-6}$-alkyl") designates saturated, straight-chain or branched hydrocarbon radicals and may be optionally substituted. The term "$C_{x-y}$-alkyl" (x and y each being an integer) refers to an alkyl group as defined before containing x to y carbon atoms. For example a $C_{1-6}$-alkyl group contains one to six carbon atoms. Representative examples of alkyl groups include methyl, ethyl, n-propyl, iso-propyl, n-butyl, iso-butyl, sec-butyl, tert-butyl, n-pentyl, n-hexyl and the like.

The term "alkenyl", taken alone or in combinations, designates straight chain or branched hydrocarbon radicals containing at least one or, depending on the chain length, up to four olefinic double bonds. Such alkenyl moieties are optionally substituted and can independently exist as E or Z configurations per double bond, which are all part of the invention. The term "$C_{x-y}$-alkenyl" (x and y each being an integer) refers to an alkenyl group as defined before containing x to y carbon atoms.

The term "alkynyl" designates straight chain or branched hydrocarbon radicals containing at least one or, depending on the chain length, up to four triple bonds. The term "Cx-y-alkynyl" (x and y each being an integer) refers to an alkynyl group as defined before, containing x to y carbon atoms.

The term "cycloalkyl", taken alone or in combinations, refers to a saturated or partially unsaturated alicyclic moiety having from three to ten carbon atoms and may be optionally substituted. Examples of this moiety include, but are not limited to, cyclohexyl, norbornyl, decalinyl and the like.

The term "heterocycloalkyl" in "heterocycloalkyl-$C_{1-4}$-alkyl" for groups $R^8$ and $R^9$ describes independently a saturated or partially unsaturated mono- or bicyclic moiety having from three to nine ring carbon atoms and one or more ring heteroatoms selected from oxygen, sulphur or nitrogen, provided the nitrogen is not forming an amino group. The term "heterocycloalkyl" includes, for example, tetrahydrofuranyl and the like.

For all other R groups, the term "heterocycloalkyl", taken alone or in combinations, describes a saturated or partially unsaturated mono- or bicyclic moiety having from three to nine ring carbon atoms and one or more ring heteroatoms selected from nitrogen, oxygen or sulphur. This term includes, for example, morpholino, piperazino, azetidinyl, pyrrolidinyl, tetrahydrofuranyl, piperidinyl, octahydro-1H-indolyl, 1,7-diazaspiro[4.4] nonanyl and the like. Said heterocycloalkyl ring(s) might be optionally substituted.

The term "aryl", taken alone or in combinations, designates aromatic carbocyclic hydrocarbon radicals containing one or two six-membered rings, such as phenyl or naphthyl, which may be optionally substituted by up to three substituents such as Br, Cl, F, $CF_3$, OH, $OCF_3$, $OCHF_2$, $NH_2$, $N(CH_3)_2$, $NO_2$, CN, $C_{1-6}$-alkyl, $C_{2-6}$-alkenyl, phenyl or phenoxy.

The term "heteroaryl", taken alone or in combinations, designates aromatic heterocyclic radicals containing one or two five- and/or six-membered rings, at least one of them containing up to three heteroatoms selected from the group consisting of O, S and N and whereby the heteroaryl radicals or tautomeric forms thereof may be attached via any suitable atom. Said heteroaryl ring(s) are optionally substituted, e.g. as indicated above for "aryl".

The term "aryl-$C_{x-y}$-alkyl", as used herein, refers to an $C_{x-y}$-alkyl group as defined above, substituted by an aryl group, as defined above. Representative examples of aryl-$C_{x-y}$-alkyl moieties include, but are not limited to, benzyl, 1-phenylethyl, 2-phenylethyl, 3-phenylpropyl, 2-phenylpropyl and the like.

The term "heteroaryl-$C_{x-y}$-alkyl", as used herein, refers to an $C_{x-y}$-alkyl group as defined above, substituted by a heteroaryl group, as defined above. Examples of heteroaryl-$C_{x-y}$-alkyl groups include pyridin-3-ylmethyl, (1H-pyrrol-2-yl)ethyl and the like.

The term "aryl-cycloalkyl", as used herein, refers to a cycloalkyl group as defined above, substituted or annelated by an aryl group, as defined above. Examples of aryl-cycloalkyl moieties include, but are not limited to, phenyl-cyclopentyl, 2,3-dihydro-1H-indenyl, 1,2,3,4-tetrahydronaphthalenyl and the like.

The term "aryl-heterocycloalkyl", as used herein, refers to a heterocycloalkyl group as defined above, substituted or annelated by an aryl group, as defined above. Examples of aryl-heterocycloalkyl moieties include, but are not limited to, indolinyl, 1,2,3,4-tetrahydroquinolinyl and the like.

The term "heteroaryl-cycloalkyl", as used herein, refers to a cycloalkyl group as defined above, substituted or annelated by a heteroaryl group, as defined above. Examples of heteroaryl-cycloalkyl moieties include, but are not limited to, 5,6,7,8-tetrahydroquinolinyl and the like.

The term "heteroaryl-heterocycloalkyl", as used herein, refers to a heterocycloalkyl group as defined above, substituted or annelated by a heteroaryl group, as defined above. Examples of heteroaryl-heterocycloalkyl moieties include, but are not limited to, 4-(thiazol-2-yl)piperazinyl, 5,6,7,8-tetrahydro-1,6-naphthyridinyl and the like.

The terms "cycloalkyl-aryl", "heterocycloalkyl-aryl", "cycloalkyl-heteroaryl", and "heterocycloalkyl-heteroaryl", as used herein, are defined analogously to the terms "aryl-cycloalkyl", "aryl-heterocycloalkyl", "heteroaryl-cycloalkyl" and "heteroaryl-heterocycloalkyl", as defined above, but connected in the opposite direction, e.g. instead of 4-(thiazol-2-yl)piperazinyl the term refers to 2-(piperazin-1-yl)thiazolyl and the like.

The terms "hydroxy", "alkoxy" and "aryloxy", taken alone or in combinations, refer to the groups of —OH, —O-alkyl and —O-aryl respectively, wherein an alkyl group or an aryl group is as defined above. The term "$C_{x-y}$-alkoxy" (x and y each being an integer) refers to an —O-alkyl group as defined before containing x to y carbon atoms attached to an oxygen atom. Representative examples of alkoxy groups include methoxy, ethoxy, n-propoxy, isopropoxy, n-butoxy, tert-butoxy and the like. Examples of aryloxy include e.g. phenoxy. For avoidance of doubt e.g. the term "hydroxy-$C_{1-8}$-alkyl" represents, among others, groups like e.g. hydroxymethyl, 1-hydroxypropyl, 2-hydroxypropyl or 3-hydroxy-2,3-dinnethylbutyl.

The term "optionally substituted" is in general intended to mean that a group, such as, but not limited to $C_{x-y}$-alkyl, $C_{x-y}$-alkenyl, cycloalkyl, aryl, heteroaryl, heterocycloalkyl, $C_{x-y}$-alkoxy and aryloxy may be substituted with one or more substituents independently selected from amino (—$NH_2$), dimethylamino, nitro (—$NO_2$), halogen (F, Cl, Br, I), $CF_3$, cyano (—CN), hydroxy, methoxy, ethoxy, phenyloxy, benzyloxy, acetoxy, oxo (=O), carboxy, carboxamido, methyl, ethyl, phenyl, benzyl, sulfonic acid, sulfate, phosphonic acid, phosphate, or phosphonate.

In the context of this invention the term "naturally or non-naturally occurring α-amino acid" typically comprises any natural α-amino acid, such as the proteogenic amino acids (examples listed below), their natural or semi-synthetic derivatives and as well α-amino acids of purely synthetic origin. This term includes as well α-amino acid which are optionally substituted at the α-nitrogen of the amino acid such as, but not limited to, acetylation or alkylation, e.g. methylation, or benzylation.

For the avoidance of doubt the term "heteroatom" refers to any atom that is not carbon or hydrogen. The descriptors L respectively D refer to the designation of stereochemical configurations of α-amino acids and are used according the Fischer-Rosanoff convention of the IUPAC.

A further embodiment of the invention relates to derivatives of general formula (I), wherein specifically
$T^1$ is $^D$Pro; $^D$Azt; $^D$Pro(5,5Me$_2$); $^D$Pro((4S)NH$_2$); $^D$Pro((4R)NH$_2$); $^D$Pro((3R)OH); $^D$Pro((3S)OH); $^D$Pro((4R)OH); or $^D$Pro((4S)OH);
$T^2$ is Aib; Deg; Dpg; Ac4c; 3,3-AC-OXT; Cyp; Chx; Chx(4oxo); 4,4-AC-THP; Ac7c; Ac8c; Atc; or Ind;
or pharmaceutically acceptable salts thereof.

A further embodiment of the invention relates to derivatives of general formula (I), wherein specifically
$T^1$ is $^D$Pro; $^D$Azt; $^D$Pro(5,5Me$_2$); or $^D$Pro((4S)NH$_2$);
$T^2$ is Aib; Deg; Dpg; Ac4c; 3,3-AC-OXT; Cyp; Chx; 4,4-AC-THP; Ac7c; Ac8c; or Ind;
or pharmaceutically acceptable salts thereof.

A further embodiment of the invention relates to derivatives of general formula (I), wherein specifically
$T^1$ is $^D$Pro; or $^D$Pro(5,5Me$_2$);
$T^2$ is Aib; Deg; Dpg; Ac4c; 3,3-AC-OXT; Cyp; Chx; 4,4-AC-THP; Ac7c; Ac8c; or Ind;
or pharmaceutically acceptable salts thereof.

A further embodiment of the invention relates to derivatives of general formula (I), wherein specifically
$T^1$ is $^D$Pro; $^D$Azt; $^D$Pro(5,5Me$_2$); $^D$Pro((4S)NH$_2$); $^D$Pro((4R)NH$_2$); $^D$Pro((3R)OH); $^D$Pro((3S)OH); $^D$Pro((4R)OH); or $^D$Pro((4S)OH);
$T^2$ is Aib; Deg; Dpg; Ac4c; 3,3-AC-OXT; Cyp; Chx; Chx(4oxo); 4,4-AC-THP; Ac7c; Ac8c; Atc; or Ind;
$P^1$ is Phe; Tyr; 3Pal; 2Thi; or 3Thi;
$P^2$ is Asp; Asn; Glu; Hgl; Gln; hGln; Cit; Bbta; 2Pal; 3Pal; 4Pal; h2Pal; h3Pal; h4Pal; Ala(2Furyl); Ala(3Furyl); Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); Ala(4Quin); Phe; Phe(4NH$_2$); Phe(mC(NH$_2$)=NH); Phe(pC(NH$_2$)=NH); Phe(2Cl); Phe(3Cl); Phe(4Cl); Phe(3,4Cl$_2$); Phe(2F); Phe(3F); Phe(4F); Phe(3CN); Phe(4CN); Phe(2CF$_3$); Phe(3CF$_3$); Phe(4CF$_3$); Phe(3,4(CF$_3$)$_2$); Phe(4COOMe); hPhe; Phg; 1Nal; 2Nal; Nle(6OBn); Ser(Bn); Thr(Bn); Trp; Trp(7Aza); Trp(5Br); Trp(6Br); Trp(6CF$_3$); Trp(5Cl); Trp(6Cl); Trp(5,6Cl); Trp(5OH); hTrp; His; His(Me); His(Bn); hHis; 2Thi; 3Thi; Tyr; Tyr(3F); Tyr(Bn); Tyr(Me); Tyr(Ph); Tyr(4OHPh); hTyr; or Tza;
$P^3$ is Leu; Nle; Cha; Chg; Asn; Gln; hGln; or Cit;
$P^4$ is Leu; Nle; Val; Bbta; 2Pal; 3Pal; 4Pal; h2Pal; h3Pal; h4Pal; Ala(2Furyl); Ala(3Furyl); Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); Ala(4Quin); Phe; Phe(4NH$_2$); Phe(mC(NH$_2$)=NH); Phe(pC(NH$_2$)=NH); Phe(2Cl); Phe(3Cl); Phe(4Cl); Phe(3,4Cl$_2$); Phe(2F); Phe(3F); Phe(4F); Phe(3CN); Phe(4CN); Phe(2CF$_3$); Phe(3CF$_3$); Phe(4CF$_3$); Phe(3,4(CF$_3$)$_2$); Phe(4COOMe); hPhe; Phg; 1Nal; 2Nal; Nle(6OBn); Ser(Bn); Thr(Bn); Trp; Trp(7Aza); Trp(5Br); Trp(6Br); Trp(6CF$_3$); Trp(5Cl); Trp(6Cl); Trp(5,6Cl);Trp(5OH); hTrp; His; His(Me); His(Bn); hHis; 2Thi; 3Thi; Tyr; Tyr(3F); Tyr(Bn); Tyr(Me); Tyr(Ph); Tyr(4OHPh); hTyr; or Tza;
$P^5$ is Ala; Aib; or Abu;
$P^6$ is Trp; Trp(5OH); Tpi; or Trp(1Me);
$P^7$ is Asp; Asn; Glu; Hgl; Gln; hGln; or Cit;
$P^8$ is Bbta; 2Pal; 3Pal; 4Pal; h2Pal; h3Pal; h4Pal; Ala(2Furyl); Ala(3Furyl); Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); Ala(4Quin); Phe; Phe(4NH$_2$); Phe(mC(NH$_2$)=NH); Phe(pC(NH$_2$)=NH); Phe(2Cl); Phe(3Cl); Phe(4Cl); Phe(3,4Cl$_2$); Phe(2F); Phe(3F); Phe(4F); Phe(3CN); Phe(4CN); Phe(2CF$_3$); Phe(3CF$_3$); Phe(4CF$_3$); Phe(3,4(CF$_3$)$_2$); Phe(4COOMe); hPhe; Phg; 1Nal; 2Nal; Nle(6OBn); Ser(Bn); Thr(Bn); Trp; Trp(7Aza); Trp(5Br);Trp(6Br); Trp(6CF$_3$); Trp(5Cl); Trp(6Cl); Trp(5,6Cl); Trp(5OH); hTrp; His; His(Me); His(Bn); hHis; 2Thi; 3Thi; Tyr; Tyr(3F); Tyr(Bn); Tyr(Me); Tyr(Ph); Tyr(4OHPh); hTyr; Tza; Arg; hArg; Agp; Lys; hLys; or Orn;
with the proviso that
if $P^3$ is Asn; Gln; hGln; or Cit; then
  $P^2$ is Bbta; 2Pal; 3Pal; 4Pal; h2Pal; h3Pal; h4Pal; Ala(2Furyl); Ala(3Furyl); Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); Ala(4Quin); Phe; Phe(4NH$_2$); Phe(mC(NH$_2$)=NH); Phe(pC(NH$_2$)=NH); Phe(2Cl); Phe(3Cl); Phe(4Cl); Phe(3,4Cl$_2$); Phe(2F); Phe(3F); Phe(4F); Phe(3CN); Phe(4CN); Phe(2CF$_3$); Phe(3CF$_3$); Phe(4CF$_3$); Phe(3,4(CF$_3$)$_2$); Phe(4COOMe); hPhe; Phg; 1Nal; 2Nal; Nle(6OBn); Ser(Bn); Thr(Bn); Trp; Trp(7Aza); Trp(5Br); Trp(6Br); Trp(6CF$_3$); Trp(5Cl); Trp(6Cl); Trp(5,6Cl); Trp(5OH); hTrp; His; His(Me); His(Bn); hHis; 2Thi; 3Thi; Tyr; Tyr(3F); Tyr(Bn); Tyr(Me); Tyr(Ph); Tyr(4OHPh); hTyr; or Tza;
  $P^7$ is Asp; Glu; Hgl; or Cit;
or if $P^3$ is Leu; Nle; Cha; or Chg; then
  $P^2$ is Asp; Asn; Glu; Hgl; Gln; hGln; Cit; Bbta; 2Pal; 3Pal; 4Pal; h2Pal; h3Pal; h4Pal; Ala(2Furyl); Ala(3Furyl); Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); Ala(4Quin); Phe; Phe(4NH$_2$); Phe(mC(NH$_2$)=NH); Phe(pC(NH$_2$)=NH); Phe(2Cl); Phe(3Cl); Phe(4Cl); Phe(3,4Cl$_2$); Phe(2F); Phe(3F);

Phe(4F); Phe(3CN); Phe(4CN); Phe(2CF$_3$); Phe (3CF$_3$); Phe(4CF$_3$); Phe(3,4(CF$_3$)$_2$); Phe(4COOMe); hPhe; Phg; 1Nal; 2Nal; Nle(6OBn); Ser(Bn); Thr(Bn); Trp; Trp(7Aza); Trp(5Br); Trp(6Br); Trp(6CF$_3$); Trp (5Cl); Trp(6Cl); Trp(5,6Cl); Trp(5OH); hTrp; His; His (Me); His(Bn); hHis; 2Thi; 3Thi; Tyr; Tyr(3F); Tyr (Bn); Tyr(Me); Tyr(Ph); Tyr(4OHPh); hTyr; or Tza;
and with the further proviso that
if P$^2$ is Asn; Gln; hGln; Cit; Bbta; 2Pal; 3Pal; 4Pal; h2Pal; h3Pal; h4Pal; Ala(2Furyl); Ala(3Furyl); Ala (1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala (2Quin); Ala(3Quin); Ala(4Quin); Phe; Phe(4NH$_2$); Phe(mC(NH$_2$)=NH); Phe(pC(NH$_2$)=NH); Phe (2Cl); Phe(3Cl); Phe(4Cl); Phe(3,4Cl$_2$); Phe(2F); Phe(3F); Phe(4F); Phe(3CN); Phe(4CN); Phe (2CF$_3$); Phe(3CF$_3$); Phe(4CF$_3$); Phe(3,4(CF$_3$)$_2$); Phe (4COOMe); hPhe; Phg; 1Nal; 2Nal; Nle(6OBn); Ser(Bn); Thr(Bn); Trp; Trp(7Aza); Trp(5Br); Trp (6Br); Trp(6CF$_3$); Trp(5Cl); Trp(6Cl); Trp(5,6Cl); Trp(5OH); hTrp; His; His(Me); His(Bn); hHis; 2Thi; 3Thi; Tyr; Tyr(3F); Tyr(Bn); Tyr(Me); Tyr(Ph); Tyr (4OHPh); hTyr; or Tza; then
P$^7$ is Glu; or Hgl;
or a pharmaceutically acceptable salt thereof.

A further embodiment of the invention relates to derivatives of general formula (I), wherein specifically
P$^1$ is $^D$Pro; $^D$Azt; $^D$Pro(5,5Me$_2$); or $^D$Pro((4S)NH$_2$);
T$^2$ is Aib; Deg; Dpg; Ac4c; 3,3-AC-OXT; Cyp; Chx; 4,4-AC-THP; Ac7c; Ac8c; or Ind;
P$^1$ is Phe; 3Pal; 2Thi; or 3Thi;
P$^2$ is Glu; Hgl; Gln; Cit; Phe; Phe(4NH$_2$); Phe(4F); Phe (4Cl); 3Pal; 4Pal; Tyr; Tyr(Me); Tyr(Ph); Tyr(Bn); His; His(Bn); Trp; or Trp(5OH);
P$^3$ is Leu; Nle; Cha; Chg; Gln; or Cit;
P$^4$ is Leu; Nle; Val; Phe; hPhe; Phe(4NH$_2$); Phe(4Cl); Phe(4CN); 4Pal; Tyr; Tyr(Me); Tyr(Ph); His; or 2Thi;
P$^5$ is Ala; Aib; or Abu;
P$^6$ is Trp; or Trp(1Me);
P$^7$ is Asp; Glu; Hgl; Gln; or Cit;
P$^8$ is Phe; Phg; hPhe; Phe(4NH$_2$); Phe(3Cl); Phe(4Cl); Phe(4CN); 3Pal; Tyr; Tyr(Me); Tyr(Bn); His; His(Bn); 2Thi; 3Thi; Trp; Trp(5OH); Arg; or Lys;
with the proviso that
P$^3$ is Gln; or Cit; then
P$^2$ is Phe; Phe(4NH$_2$); Phe(4F); Phe(4Cl); 3Pal; 4Pal; Tyr; Tyr(Me); Tyr(Ph); Tyr(Bn); His; His(Bn); Trp; or Trp (5OH);
P$^7$ is Asp; Glu; Hgl; or Cit;
or if P$^3$ is Leu; Nle; Cha; or Chg; then
P$^2$ is Glu; Hgl; Gln; Cit; Phe; Phe(4NH$_2$); Phe(4F); Phe(4Cl); 3Pal; 4Pal; Tyr; Tyr(Me); Tyr(Ph); Tyr(Bn); His; His(Bn); Trp; or Trp(5OH);
and with the further poviso that
if P$^2$ is Gln; Cit; Phe; Phe(4NH$_2$); Phe(4F); Phe(4Cl); 3Pal; 4Pal; Tyr; Tyr(Me); Tyr(Ph); Tyr(Bn); His; His(Bn); Trp; or Trp(5OH); then P$^7$ is Glu; or Hgl;
or a pharmaceutically acceptable salt thereof.

A further embodiment of the invention relates to derivatives of general formula (I), wherein specifically
T$^1$ is $^D$Pro; or $^D$Pro(5,5Me2);
T$^2$ is Aib; Deg; Dpg; Ac4c; 3,3-AC-OXT; Cyp; Chx; 4,4-AC-THP; Ac7c; Ac8c; or Ind;
P$^1$ is Phe; 3Pal; 2Thi; or 3Thi;

P$^2$ is Glu; Hgl; Gln; Cit; Phe; Phe(4NH$_2$); Phe(4F); Phe (4Cl); 3Pal; 4Pal; Tyr; Tyr(Me); Tyr(Ph); Tyr(Bn); His; His(Bn); Trp; or Trp(5OH);
P$^3$ is Leu; Nle; Cha; Chg; Gln; or Cit;
P$^4$ is Leu; Nle; Val; Phe; hPhe; Phe(4NH$_2$); Phe(4Cl); Phe(4CN); 4Pal; Tyr; Tyr(Me); Tyr(Ph); His; or 2Thi;
P$^5$ is Ala; Aib; or Abu;
P$^6$ is Trp; or Trp(1Me);
P$^7$ is Asp; Glu; Hgl; Gln; or Cit;
P$^8$ is Phe; Phg; hPhe; Phe(4NH$_2$); Phe(3Cl); Phe(4Cl); Phe(4CN); 3Pal; Tyr; Tyr(Me); Tyr(Bn); His; His(Bn); 2Thi; 3Thi; Trp; Trp(5OH); Arg; or Lys;
with the proviso that
if P$^3$ is Gln; or Cit; then
P$^2$ is Phe; Phe(4NH$_2$); Phe(4F); Phe(4Cl); 3Pal; 4Pal; Tyr; Tyr(Me); Tyr(Ph); Tyr(Bn); His; His(Bn); Trp; or Trp (5OH);
P$^7$ is Asp; Glu; Hgl; or Cit;
or if P$^3$ is Leu; Nle; Cha; or Chg; then
P$^2$ is Glu; Hgl; Gln; Cit; His; or Trp;
and with the further proviso that
if P$^2$ is Gln; Cit; His; or Trp; then
P$^7$ is Glu; or Hgl;
or a pharmaceutically acceptable salt thereof.

Another embodiment of the invention relates to derivatives of general formula (I), wherein specifically
T$^1$ is $^D$Pro;
T$^2$ is Aib; Deg; Dpg; Cyp; Chx; Ac7c; Ac8c; or Ind;
P$^1$ is Phe;
P$^2$ is Glu; Gln; Phe; Phe(4NH$_2$); 3Pal; 4Pal; Tyr; Tyr(Me); Tyr(Ph); Tyr(Bn); His; His(Bn); Trp; or Trp(5OH);
P$^3$ is Leu; or Gln;
P$^4$ is Leu; Phe; Phe(4CN); Tyr; or Tyr(Me);
P$^5$ is Ala;
P$^6$ is Trp;
P$^7$ is Glu; Hgl; Gln; or Cit;
P$^8$ is Phe; Phg; Phe(4NH$_2$); 3Pal; Tyr; Tyr(Me); Tyr(Bn); His; His(Bn); Trp; Trp(5OH); or Arg;
with the proviso that
if P$^3$ is Gln; then
P$^2$ is Phe; Phe(4NH$_2$); 3Pal; 4Pal; Tyr; Tyr(Me); Tyr(Ph); Tyr(Bn); His; His(Bn); Trp; or Trp(5OH);
P$^7$ is Glu; Hgl; or Cit;
or if P$^3$ is Leu; then
P$^2$ is Glu; Gln; His; or Trp;
P$^7$ is Glu; Hgl; Gln; or Cit;
and with the further proviso that
if P$^2$ is Gln; His; or Trp; then
P$^7$ is Glu; or Hgl;
or a pharmaceutically acceptable salt thereof.

Another embodiment of the invention relates to derivatives of general formula (I), wherein specifically
T$^1$ is $^D$Pro;
T$^2$ is Aib; Deg; Dpg; Cyp; Chx; Ac7c; Ac8c; or Ind;
P$^1$ is Phe;
P$^2$ is Phe; Phe(4NH$_2$); 3Pal; 4Pal; Tyr; Tyr(Me); Tyr(Ph); Tyr(Bn); His; His(Bn); Trp; or Trp(5OH);
P$^3$ is Leu; or Gln;
P$^4$ is Leu; Phe; Phe(4CN); Tyr; or Tyr(Me);
P$^5$ is Ala;
P$^6$ is Trp;
P$^7$ is Glu; Hgl; Gln; or Cit;
P$^8$ is Phe; Phg; Phe(4NH$_2$); 3Pal; Tyr; Tyr(Me); Tyr(Bn); His; His(Bn); Trp; Trp(5OH); or Arg;

with the proviso that
if $P^3$ is Gln; then
  $P^2$ is Phe; Phe(4NH$_2$); 3Pal; 4Pal; Tyr; Tyr(Me); Tyr(Ph); Tyr(Bn); His; His(Bn); Trp; or Trp(5OH);
  $P^7$ is Glu; Hgl; or Cit;
or if $P^3$ is Leu; then
  $P^2$ is His; or Trp;
  $P^7$ is Glu; or Hgl;
or a pharmaceutically acceptable salt thereof.

Another embodiment of the invention relates to derivatives of general formula (I), wherein specifically
$T^1$ is $^D$Pro;
$T^2$ is Aib; Cyp; Chx; or Ind;
$P^1$ is Phe;
$P^2$ is Glu; Phe; Phe(4NH$_2$); 3Pal; 4Pal; Tyr; Tyr(Me); Tyr(Ph); Tyr(Bn); His; His(Bn); or Trp;
$P^3$ is Leu; or Gln;
$P^4$ is Leu; Phe; Phe(4CN); Tyr; or Tyr(Me);
$P^5$ is Ala;
$P^6$ is Trp;
$P^7$ is Glu; or Cit;
$P^8$ is Phe; Phe(4NH$_2$); 3Pal; Tyr; Tyr(Me); Tyr(Bn); His(Bn); Trp; Trp(5OH); or Arg;
with the proviso that
if $P^3$ is Gln; then
  $P^2$ is Phe; Phe(4NH$_2$); 3Pal; 4Pal; Tyr; Tyr(Me); Tyr(Ph); Tyr(Bn); His; His(Bn); or Trp;
or if $P^3$ is Leu; then
  $P^2$ is Glu; His; or Trp;
  and with the further proviso that
    if $P^2$ is His; or Trp; then
      $P^7$ is Glu;
or a pharmaceutically acceptable salt thereof.

Another embodiment of the invention relates to derivatives of general formula (I), wherein specifically
$T^1$ is $^D$Pro;
$T^2$ is Aib; Deg; Dpg; Cyp; Chx; Ac7c; Ac8c; or Ind;
$P^1$ is Phe;
$P^2$ is Phe; Phe(4NH$_2$); 3Pal; 4Pal; Tyr; Tyr(Me); Tyr(Ph); Tyr(Bn); His; His(Bn); or Trp;
$P^3$ is Leu; or Gln;
$P^4$ is Phe; Tyr; or Tyr(Me);
$P^5$ is Ala;
$P^6$ is Trp;
$P^7$ is Glu;
$P^8$ is Phe; Phe(4NH$_2$); Tyr; Tyr(Me); Tyr(Bn); His(Bn); Trp; Trp(5OH); or Arg;
with the proviso that
if $P^3$ is Leu; then
  $P^2$ is His or Trp;
or a pharmaceutically acceptable salt thereof.

Another embodiment of the invention relates to derivatives of general formula (I), wherein specifically
$T^1$ is $^D$Pro;
$T^2$ is Aib; or Chx;
$P^1$ is Phe;
$P^2$ is Phe; Phe(4NH$_2$); 3Pal; 4Pal; Tyr; Tyr(Me); Tyr(Ph); Tyr(Bn); His; His(Bn); or Trp;
$P^3$ is Leu; or Gln;
$P^4$ is Phe; Tyr; or Tyr(Me);
$P^5$ is Ala;
$P^6$ is Trp;
$P^7$ is Glu;
$P^8$ is Phe; Phe(4NH$_2$); Tyr; Tyr(Me); Tyr(Bn); His(Bn); Trp; Trp(5OH); or Arg;
with the proviso that
if $P^3$ is Leu; then
  $P^2$ is His or Trp;
or a pharmaceutically acceptable salt thereof.

Another embodiment of the invention relates to derivatives of general formula (I), wherein specifically
$T^1$ is $^{oD}$Pro;
$T^2$ is Chx;
$P^1$ is Phe;
$P^2$ is Phe; Phe(4NH$_2$); 3Pal; Tyr(Ph); Tyr(Bn); His(Bn); or Trp;
$P^3$ is Gln;
$P^4$ is Tyr; or Tyr(Me);
$P^5$ is Ala;
$P^6$ is Trp;
$P^7$ is Glu;
$P^8$ is Tyr; or Arg;
or a pharmaceutically acceptable salt thereof.

Hereinafter follows a list of abbreviations, corresponding to generally adopted usual practice, of amino acids which, or the residues of which, are suitable for the purposes of the present invention and referred to in this document.

In spite of this specific determination of amino acids, it is noted that, for a person skilled in the art, it is obvious that derivatives of these amino acids, resembling alike structural and physico-chemical properties, lead to functional analogues with similar biological activity, and therefore still form part of the gist of this invention.

Ala L-Alanine
Arg L-Arginine
Asn L-Asparagine
Asp L-Aspartic acid
Cit L-Citrulline
Cys L-Cysteine
Gln L-Glutamine
Glu L-Glutamic acid
Gly Glycine
His L-Histidine
Ile L-Isoleucine
Leu L-Leucine
Lys L-Lysine
Met L-Methionine
Orn L-Ornithine
Phe L-Phenylalanine
Pro L-Proline
Ser L-Serine
Thr L-Threonine
Trp L-Tryptophan
Tyr L-Tyrosine
Val L-Valine
Abu (S)-2-aminobutanoic acid
3,3-AC-OXT 3-aminooxetane-3-carboxylic acid
4,4-AC-THP 4-aminotetrahydro-2H-pyran-4-carboxylic acid
Ac4c 1-aminocyclobutane carboxylic acid
Ac7c 1-aminocycloheptane carboxylic acid
Ac8c 1-aminocyclooctane carboxylic acid
Agp (S)-2-amino-3-guanidinopropanoic acid
Aib 2-methyl-2-aminopropanoic acid
Ala(1Im) (S)-2-amino-3-(1H-imidazol-1-yl)propanoic acid
Ala(2Im) (S)-2-amino-3-(1H-imidazol-2-yl)propanoic acid
Ala(Pyrazinyl) (S)-2-amino-3-(pyrazin-2-yl)propanoic acid
Ala(1Pyrazolyl) (S)-2-amino-3-(1H-pyrazol-1-yl)propanoic acid
Ala(3Pyrazolyl) (S)-2-amino-3-(1H-pyrazol-3-yl)propanoic acid
Ala(2Pyrimidin) (S)-2-amino-3-(pyrimidin-2-yl)propanoic acid Ala(4Pyrimidin) (S)-2-amino-3-(pyrimidin-4-yl)propanoic acid
Ala(5Pyrimidin) (S)-2-amino-3-(pyrimidin-5-yl)propanoic acid
Ala(2Quin) (S)-2-amino-3-(quinolin-2-yl)propanoic acid
Ala(3Quin) (S)-2-amino-3-(quinolin-3-yl)propanoic acid
Ala(4Quin) (S)-2-amino-3-(quinolin-4-yl)propanoic acid
Atc (S)-2-amino-1,2,3,4-tetrahydronaphthalene-2-carboxylic acid
Azt (2S)-azetidine-2-carboxylic acid
Bbta (S)-2-amino-3-(1-benzothiophen-3-yl)propanoic acid
Cha (S)-2-amino-3-cyclohexylpropanoic acid
Chg (S)-2-amino-2-cyclohexylacetic acid
Chx 1-aminocyclohexane carboxylic acid
Chx(4oxo) 1-amino-4-oxo-cyclohexane carboxylic acid
Cyp 1-aminocyclopentane carboxylic acid
Deg 2-amino-2-ethylbutanoic acid
Dpg 2-amino-2-propylpentanoic acid
hAla(1Im) (S)-2-amino-3-(1H-imidazol-1-yl)-butanoic acid
hAla(2Im) (S)-2-amino-3-(1H-imidazol-2-yl)-butanoic acid
hArg (S)-2-amino-6-guanidinohexanoic acid
hHis (S)-2-amino-4-(1H-imidazol-5-yl)butanoic acid
hLys (S)-2,7-diaminoheptanoic acid
h2Pal (S)-2-amino-4-(pyridin-2-yl)-butanoic acid
h3Pal (S)-2-amino-3-(pyridine-3-yl)-butanoic acid
h4Pal (S)-2-amino-3-(pyridine-4-yl)-butanoic acid
hGln (S)-2,6-diamino-6-oxohexanoic acid
hPhe (S)-2-amino-4-phenylbutanoic acid
hSer (S)-2-amino-4-hydroxybutanoic acid
hTrp (S)-2-amino-4-(1H-indol-3-yl)butanoic acid
hTyr (S)-2-amino-4-(4-hydroxyphenyl)butanoic acid
Hgl (S)-2-aminoadipic acid
His(Me) (S)-2-amino-3-(1-methyl-1H-imidazol-5-yl)propanoic acid
His(Bn) (S)-2-amino-3-(1-benzyl-1H-imidazol-5-yl)propanoic acid
Ind 2-amino-indan-2-carboxylic acid
1Nal (S)-2-amino-3-naphthalen-1-ylpropanoic acid
2Nal (S)-2-amino-3-naphthalen-2-ylpropanoic acid
Nle (S)-2-amino-hexanoic acid
2Pal (S)-2-amino-3-(pyridine-2-yl) propionic acid
3Pal (S)-2-amino-3-(pyridine-3-yl)propionic acid
4Pal (S)-2-amino-3-(pyridine-4-yl)propionic acid
Phe(2Cl) (S)-2-amino-3-(2-chlorophenyl)propanoic acid
Phe(3Cl) (S)-2-amino-3-(3-chlorophenyl)propanoic acid
Phe(4Cl) (S)-2-amino-3-(4-chlorophenyl)propanoic acid
Phe(3,4Cl) (S)-2-amino-3-(3,4-dichlorophenyl)propanoic acid
Phe(2F) (S)-2-amino-3-(2-fluorophenyl)propanoic acid
Phe(3F) (S)-2-amino-3-(3-fluorophenyl)propanoic acid
Phe(4F) (S)-2-amino-3-(4-fluorophenyl)propanoic acid
Phe(3,4F$_2$) (S)-2-amino-3-(3,4-difluorophenyl)propanoic acid
Phe(2CN) (S)-2-amino-3-(2-cyanophenyl)propanoic acid
Phe(3CN) (S)-2-amino-3-(3-cyanophenyl)propanoic acid
Phe(4CN) (S)-2-amino-3-(4-cyanophenyl)propanoic acid
Phe(2CF$_3$) (S)-2-amino-3-(2-(trifluoromethyl)phenyl)propanoic acid
Phe(3CF$_3$) (S)-2-amino-3-(3-(trifluoromethyl)phenyl)propanoic acid
Phe(4CF$_3$) (S)-2-amino-3-(4-(trifluoromethyl)phenyl)propanoic acid
Phe(3,4(CF$_3$)$_2$) (S)-2-amino-3-(3,4-bis(trifluoromethyl)phenyl)propanoic acid
Phe(4COOMe) (S)-2-amino-3-(4-(methoxycarbonyl)phenyl)propanoic acid
Phe(4NH$_2$) (S)-2-amino-3-(4-aminophenyl)propanoic acid
Phe(mC(NH$_2$)=NH) (S)-2-amino-3-(3-amidinophenyl)-propanoic acid
Phe(pC(NH$_2$)=NH) (S)-2-amino-3-(4-amidinophenyl)-propanoic acid
Phg (S)-2-amino-2-phenylacetic acid
Pro(5,5Me$_2$) (S)-5,5-dimethylpyrrolidine-2-carboxylic acid
Pro((4R)NH$_2$) (2S,4R)-4-aminopyrrolidine-2-carboxylic acid
Pro((4S)NH$_2$) (2S,4S)-4-aminopyrrolidine-2-carboxylic acid
Pro((3R)OH) (2S,3R)-3-hydroxypyrrolidine-2-carboxylic acid
Pro((3S)OH) (2S,3S)-3-hydroxypyrrolidine-2-carboxylic acid
Pro((4R)OH) (2S,4R)-4-hydroxypyrrolidine-2-carboxylic acid
Pro((4S)OH) (2S,4S)-4-hydroxypyrrolidine-2-carboxylic acid
Ser(Bn) (S)-2-amino-3-(benzyloxy)propanoic acid
2Thi (S)-2-amino-3-(thiophen-2-yl)propanoic acid
3Thi (S)-2-amino-3-(thiophen-3-yl)propanoic acid
Thr(Bn) (2S,3R)-2-amino-3-(benzyloxy)butanoic acid
Tpi (3S)-1,2,3,4-tetrahydronorharman-3-carboxylic acid
Trp(7Aza) (S)-2-amino-3-(1H-pyrrolo[2,3-b]pyridin-3-yl) propanoic acid
Trp(5Br) (S)-2-amino-3-(5-bromo-1H-indol-3-yl)propanoic acid
Trp(6Br) (S)-2-amino-3-(6-bromo-1H-indol-3-yl)propanoic acid
Trp(6CF$_3$) (S)-2-amino-3-(6-(trifluoromethyl)-1H-indol-3-yl)propanoic acid
Trp(5Cl) (S)-2-amino-3-(5-chloro-1H-indol-3-yl)propanoic acid
Trp(6Cl) (S)-2-amino-3-(6-chloro-1H-indol-3-yl)propanoic acid
Trp(5,6Cl) (S)-2-amino-3-(5,6-dichloro-1H-indol-3-yl)propanoic acid
Trp(1Me) (S)-2-amino-3-(1-methyl-1H-indol-3-yl)propanoic acid
Trp(5OH) (S)-2-amino-3-(5-hydroxy-1H-indol-3-yl)propanoic acid
Tyr(Bn) (S)-2-amino-3-(4-(benzyloxy)phenyl)propanoic acid
Tyr(Me) (S)-2-amino-3-(4-methoxyphenyl)propanoic acid
Tyr(Ph) (S)-2-amino-3-(4-phenoxyphenyl)propanoic acid
Tyr(3F) (S)-2-amino-3-(3-fluoro-4-hydroxyphenyl)propanoic acid
Tyr(4OHPh) (S)-2-amino-3-[4-(4-hydroxyphenoxy)phenyl] propanoic acid
Tza (S)-2-amino-3-(thiazol-4-yl)propanoic acid The abbreviation of a D-isomer relates to the mirror image of the appropriate amino acid described above, e.g. $^D$Lys corresponds to the (R)-isomer at the position 2 of Lys.

In a preferred embodiment of the invention the backbone-cyclized peptidomimetics of general formula (I) are selected from the group consisting of:
cyclo(-Phe-Phe-Gln-Tyr-Ala-Trp-Glu-Tyr-$^D$Pro-Chx-);
cyclo(-Phe-3Pal-Gln-Tyr-Ala-Trp-Glu-Tyr-$^D$Pro-Chx-);
cyclo(-Phe-Phe(4NH$_2$)-Gln-Tyr-Ala-Trp-Glu-Tyr-$^D$Pro-Chx-);
cyclo(-Phe-His(Bn)-Gln-Tyr-Ala-Trp-Glu-Tyr-$^D$Pro-Chx-);
cyclo(-Phe-Tyr(Bn)-Gln-Tyr-Ala-Trp-Glu-Tyr-$^D$Pro-Chx-);
cyclo(-Phe-Tyr(Ph)-Gln-Tyr-Ala-Trp-Glu-Arg-$^D$Pro-Chx-);

cyclo(-Phe-Tyr(Ph)-Gln-Tyr-Ala-Trp-Glu-Tyr-$^D$Pro-Chx-);
cyclo(-Phe-Trp-Gln-Tyr(Me)-Ala-Trp-Glu-Tyr-$^D$Pro-Chx-);
cyclo(-Phe-Trp-Gln-Tyr-Ala-Trp-Glu-Tyr(Me)-$^D$Pro-Chx-);
cyclo(-Phe-Phe-Gln-Tyr-Ala-Trp-Glu-Arg-$^D$Pro-Chx-);
cyclo(-Phe-Tyr(Ph)-Gln-Tyr-Ala-Trp-Glu-Arg-$^D$Pro-Aib-);
cyclo(-Phe-Trp-Leu-Tyr-Ala-Trp-Glu-Tyr-$^D$Pro-Chx-);
cyclo(-Phe-Glu-Leu-Tyr-Ala-Trp-Glu-Tyr-$^D$Pro-Ind-);
cyclo(-Phe-Tyr-Gln-Tyr-Ala-Trp-Glu-Tyr-$^D$Pro-Chx-);
cyclo(-Phe-Trp-Gln-Tyr-Ala-Trp-Glu-His(Bn)-$^D$Pro-Chx-);
cyclo(-Phe-Glu-Leu-Tyr-Ala-Trp-Glu-Trp-$^D$Pro-Chx-);
cyclo(-Phe-Trp-Gln-Tyr-Ala-Trp-Glu-Trp-$^D$Pro-Chx-);
cyclo(-Phe-Trp-Gln-Tyr-Ala-Trp-Glu-Trp(5OH)-$^D$Pro-Chx-);
cyclo(-Phe-3Pal-Gln-Tyr-Ala-Trp-Glu-Arg-$^D$Pro-Chx-);
cyclo(-Phe-His-Leu-Tyr-Ala-Trp-Glu-Tyr-$^D$Pro-Chx-);
cyclo(-Phe-Phe(4NH$_2$)-Gln-Tyr-Ala-Trp-Glu-Arg-$^D$Pro-Chx-);
cyclo(-Phe-Trp-Gln-Tyr-Ala-Trp-Glu-Tyr(Bn)-$^D$Pro-Chx-);
cyclo(-Phe-Trp-Gln-Tyr(Me)-Ala-Trp-Glu-Arg-$^D$Pro-Chx-);
cyclo(-Phe-Trp-Gln-Tyr-Ala-Trp-Glu-Phe-$^D$Pro-Chx-);
cyclo(-Phe-Glu-Leu-Tyr-Ala-Trp-Glu-Trp(5OH)-$^D$Pro-Chx-);
cyclo(-Phe-Glu-Leu-Leu-Ala-Trp-Glu-Phe-$^D$Pro-Dpg-);
cyclo(-Phe-Trp-Gln-Phe-Ala-Trp-Glu-Tyr-$^D$Pro-Chx-);
cyclo(-Phe-Glu-Leu-Tyr-Ala-Trp-Trp(5OH)-Tyr-$^D$Pro-Chx-);
cyclo(-Phe-Glu-Leu-Tyr(Me)-Ala-Trp-Glu-Tyr-$^D$Pro-Chx-);
cyclo(-Phe-Trp-Gln-Tyr-Ala-Trp-Glu-Phe(4NH$_2$)-$^D$Pro-Chx-);
cyclo(-Phe-Glu-Leu-Tyr-Ala-Trp-Glu-Phe-$^D$Pro-Chx-);
cyclo(-Phe-Tyr(Me)-Gln-Tyr-Ala-Trp-Glu-Tyr-$^D$Pro-Chx-);
cyclo(-Phe-4Pal-Gln-Tyr-Ala-Trp-Glu-Tyr-$^D$Pro-Chx-);
cyclo(-Phe-Glu-Leu-Tyr(Me)-Ala-Trp-Glu-Tyr(Me)-$^D$Pro-Chx-);
cyclo(-Phe-Trp(5OH)-Gln-Tyr-Ala-Trp-Glu-Tyr-$^D$Pro-Chx-);
cyclo(-Phe-Glu-Leu-Tyr-Ala-Trp-Glu-His(Bn)-$^D$Pro-Chx-);
cyclo(-Phe-Glu-Leu-Phe(4CN)-Ala-Trp-Glu-Tyr-$^D$Pro-Chx-);
cyclo(-Phe-Glu-Leu-Tyr-Ala-Trp-Cit-Tyr-$^D$Pro-Chx-);
cyclo(-Phe-Glu-Leu-Tyr-Ala-Trp-G lu-H is-$^D$P ro-Chx-);
cyclo(-Phe-Gln-Leu-Tyr-Ala-Trp-Glu-Tyr-$^D$Pro-Chx-);
cyclo(-Phe-Glu-Leu-Tyr-Ala-Trp-Glu-3Pal-$^D$Pro-Chx-);
cyclo(-Phe-Glu-Leu-Tyr-Ala-Trp-Glu-Arg-$^D$Pro-Chx-);
cyclo(-Phe-Glu-Leu-Leu-Ala-Trp-Glu-Phe-$^D$Pro-Chx-);
cyclo(-Phe-Glu-Leu-Leu-Ala-Trp-Glu-Phe-$^D$Pro-Cyp-);
cyclo(-Phe-Glu-Leu-Leu-Ala-Trp-Glu-Phe-$^D$Pro-Aib-);
cyclo(-Phe-Trp-Gln-Leu-Ala-Trp-Glu-Phe-$^D$Pro-Cyp-);
cyclo(-Phe-Glu-Leu-Leu-Ala-Trp-Glu-Phe-$^D$Pro-Deg-);
cyclo(-Phe-Glu-Leu-Tyr-Ala-Trp-Glu-Phe-$^D$Pro-Cyp-);
cyclo(-Phe-Gln-Leu-Tyr-Ala-Trp-Hgl-Tyr-$^D$Pro-Chx-);
cyclo(-Phe-Glu-Leu-Tyr-Ala-Trp-Phg-$^D$Pro-Chx-);
cyclo(-Phe-His-Leu-Tyr-Ala-Trp-Gln-Tyr-$^D$Pro-Aib-);
cyclo(-Phe-Glu-Leu-Leu-Ala-Trp-Glu-Phe-$^D$Pro-Ind-);
cyclo(-Phe-Glu-Leu-Leu-Ala-Trp-Glu-Phe-$^D$Pro-Ac7c-);
cyclo(-Phe-Glu-Leu-Leu-Ala-Trp-Glu-Phe-$^D$Pro-Ac8c-);
or pharmaceutically acceptable salts thereof.

In a preferred embodiment of the invention the backbone-cyclized peptidomimetics of general formula (I) are selected from the group consisting of:
cyclo(-Phe-Phe-Gln-Tyr-Ala-Trp-Glu-Tyr-$^D$Pro-Chx-);
cyclo(-Phe-3Pal-Gln-Tyr-Ala-Trp-Glu-Tyr-$^D$Pro-Chx-);
cyclo(-Phe-Phe(4NH$_2$)-Gln-Tyr-Ala-Trp-Glu-Tyr-$^D$Pro-Chx-);
cyclo(-Phe-His(Bn)-Gln-Tyr-Ala-Trp-Glu-Tyr-$^D$Pro-Chx-);
cyclo(-Phe-Tyr(Bn)-Gln-Tyr-Ala-Trp-Glu-Tyr-$^D$Pro-Chx-);
cyclo(-Phe-Tyr(Ph)-Gln-Tyr-Ala-Trp-Glu-Arg-$^D$Pro-Chx-);
cyclo(-Phe-Tyr(Ph)-Gln-Tyr-Ala-Trp-Glu-Tyr-$^D$Pro-Chx-);
cyclo(-Phe-Trp-Gln-Tyr(Me)-Ala-Trp-Glu-Tyr-$^D$Pro-Chx-);
cyclo(-Phe-Trp-Gln-Tyr-Ala-Trp-Glu-Tyr(Me)-$^D$Pro-Chx-);
cyclo(-Phe-Phe-Gln-Tyr-Ala-Trp-Glu-Arg-$^D$Pro-Chx-);
cyclo(-Phe-Tyr(Ph)-Gln-Tyr-Ala-Trp-Glu-Arg-$^D$Pro-Aib-);
cyclo(-Phe-Trp-Leu-Tyr-Ala-Trp-Glu-Tyr-$^D$Pro-Chx-);
cyclo(-Phe-Glu-Leu-Tyr-Ala-Trp-Glu-Tyr-$^D$Pro-Ind-);
cyclo(-Phe-Tyr-Gln-Tyr-Ala-Trp-Glu-Tyr-$^D$Pro-Chx-);
cyclo(-Phe-Trp-Gln-Tyr-Ala-Trp-Glu-His(Bn)-$^D$Pro-Chx-);
cyclo(-Phe-Glu-Leu-Tyr-Ala-Trp-Glu-Trp-$^D$Pro-Chx-);
cyclo(-Phe-Trp-Gln-Tyr-Ala-Trp-Glu-Trp-$^D$Pro-Chx-);
cyclo(-Phe-Trp-Gln-Tyr-Ala-Trp-Glu-Trp(5OH)-$^D$Pro-Chx-);
cyclo(-Phe-3Pal-Gln-Tyr-Ala-Trp-Glu-Arg-$^D$Pro-Chx-);
cyclo(-Phe-His-Leu-Tyr-Ala-Trp-Glu-Tyr-$^D$Pro-Chx-);
cyclo(-Phe-Phe(4NH$_2$)-Gln-Tyr-Ala-Trp-Glu-Arg-$^D$Pro-Chx-);
cyclo(-Phe-Trp-Gln-Tyr-Ala-Trp-Glu-Tyr(Bn)-$^D$Pro-Chx-);
cyclo(-Phe-Trp-Gln-Tyr(Me)-Ala-Trp-Glu-Arg-$^D$Pro-Chx-);
cyclo(-Phe-Trp-Gln-Tyr-Ala-Trp-Glu-Phe-$^D$Pro-Chx-);
cyclo(-Phe-Glu-Leu-Tyr-Ala-Trp-Glu-Trp(5OH)-$^D$Pro-Chx-);
cyclo(-Phe-Trp-Gln-Phe-Ala-Trp-Glu-Tyr-$^D$Pro-Chx-);
cyclo(-Phe-Glu-Leu-Tyr(Me)-Ala-Trp-Glu-Tyr-$^D$Pro-Chx-);
cyclo(-Phe-Trp-Gln-Tyr-Ala-Trp-Glu-Phe(4NH$_2$)-$^D$Pro-Chx-);
cyclo(-Phe-Glu-Leu-Tyr-Ala-Trp-Glu-Phe-$^D$Pro-Chx-);
cyclo(-Phe-Tyr(Me)-Gln-Tyr-Ala-Trp-Glu-Tyr-$^D$Pro-Chx-);
cyclo(-Phe-4Pal-Gln-Tyr-Ala-Trp-Glu-Tyr-$^D$Pro-Chx-);
cyclo(-Phe-Glu-Leu-Tyr(Me)-Ala-Trp-Glu-Tyr(Me)-$^D$Pro-Chx-);
cyclo(-Phe-Glu-Leu-Tyr-Ala-Trp-Glu-His(Bn)-$^D$Pro-Chx-);
cyclo(-Phe-Glu-Leu-Phe(4CN)-Ala-Trp-Glu-Tyr-$^D$Pro-Chx-);
cyclo(-Phe-Glu-Leu-Tyr-Ala-Trp-Cit-Tyr-$^D$Pro-Chx-);
cyclo(-Phe-Glu-Leu-Tyr-Ala-Trp-Glu-3Pal-$^D$Pro-Chx-);
cyclo(-Phe-Glu-Leu-Tyr-Ala-Trp-Glu-Phe-$^D$Pro-Cyp-);
cyclo(-Phe-Glu-Leu-Leu-Ala-Trp-Glu-Phe-$^D$Pro-Ind-);
or a pharmaceutically acceptable salt thereof.

In a particularly preferred embodiment of the invention the backbone-cyclized peptidomimetics of general formula (I) are selected from the group consisting of:

cyclo(-Phe-Phe-Gln-Tyr-Ala-Trp-Glu-Tyr-$^D$Pro-Chx-);
cyclo(-Phe-His(Bn)-Gln-Tyr-Ala-Trp-Glu-Tyr-$^D$Pro-Chx-);
cyclo(-Phe-Phe(4NH$_2$)-Gln-Tyr-Ala-Trp-Glu-Tyr-$^D$Pro-Chx-);
cyclo(-Phe-Tyr(Bn)-Gln-Tyr-Ala-Trp-Glu-Tyr-$^D$Pro-Chx-);
cyclo(-Phe-Tyr(Ph)-Gln-Tyr-Ala-Trp-Glu-Arg-$^D$Pro-Chx-);
cyclo(-Phe-3Pal-Gln-Tyr-Ala-Trp-Glu-Tyr-$^D$Pro-Chx-);
cyclo(-Phe-Trp-Gln-Tyr(Me)-Ala-Trp-Glu-Tyr-$^D$Pro-Chx-);
cyclo(-Phe-Phe-Gln-Tyr-Ala-Trp-Glu-Arg-$^D$Pro-Chx-);
or pharmaceutically acceptable salts thereof.

The peptidomimetics of the present invention can also be diastereomers (e.g. epimers) of compounds of formula (I) if no specific stereochemistry of the chiral center is determined in the description. These stereoisomers can be prepared by a modification of the process described below in which the appropriate amino acids are used.

A further embodiment of the present invention may also include compounds, which are identical to the compounds of formula (I), except that one or more atoms are replaced by an atom having an atomic mass number or mass different from the atomic mass number or mass usually found in nature, e.g. compounds enriched in, but not limited to, $^2$H (D), $^3$H, $^{11}$C, $^{14}$C, $^{127}$I. These isotopic analogs and their pharmaceutical salts and formulations are considered useful agents in the therapy and/or diagnostic, for example, but not limited to, where a fine-tuning of in vivo half-life time could lead to an optimized dosage regimen.

A further embodiment of the invention relates to the preparation of the present backbone-cyclized peptidomimetics by a process which comprises the steps of
(a) coupling an appropriately functionalized solid support with an appropriately N-protected derivative of that amino acid which in the desired end-product is in position T$^1$ or T$^2$ or P$^1$ to P$^8$ as defined above; any functional group which may be present in said N-protected amino acid derivative being likewise appropriately protected;
(b) removing the N-protecting group from the product obtained in step (a);
(c) coupling the product thus obtained with an appropriately N-protected derivative of that amino acid which in the desired end-product is in the position of the next element (T or P), following counterclockwise or clockwise the sequence according to general formula (I) in —COOH to —NH$_2$ orientation; any functional group which may be present in said N-protected amino acid derivative being likewise appropriately protected;
(d) removing the N-protecting group from the product thus obtained;
(e) repeating steps (c) and (d) until all amino acid residues have been introduced;
(f) detaching the product thus obtained from the solid support;
(g) cyclizing the product cleaved from the solid support;
(h) removing any protecting groups present on functional groups of any members of the chain of amino acid residues and, if desired, any protecting group(s) which may in addition be present in the molecule;
(i) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

The process of the invention can advantageously be carried out as parallel array synthesis to yield libraries of template-fixed backbone-cyclized peptidomimetics of the above general formula (I). Such parallel synthesis allows one to obtain arrays of numerous (normally 24 to 192, typically 96) compounds of general formula (I) in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene ("PS") crosslinked with, preferably 1-5%, divinylbenzene; polystyrene coated with polyethyleneglycol spacers (TENTAGEL®); and polyacrylamide resins (see also D. Obrecht and J. M. Villalgordo, "Solid-Supported Combinatorial and Parallel Synthesis of Small-Molecular-Weight Compound Libraries", Tetrahedron Organic Chemistry Series, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (H. Rink, *Tetrahedron Lett.* 1987, 28, 3783-3790). Linkers of this kind form amides of the carboxyl group of the amino acids; examples of resins functionalized by such linker structures include 4-[(((2,4-dimethoxyphenyl)Fmoc-aminomethyl)phenoxyacetamido)-aminomethyl] PS resin, 4-[(((2,4-dimethoxyphenyl)Fmoc-aminomethyl)phenoxyacet-amido)aminomethyl]-4-methylbenzhydrylamine PS resin (Rink amide MBHA PS Resin), and 4-[(((2,4-dimethoxyphenyl)Fmoc-aminomethyl)phenoxyacetamido)aminomethyl]-benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl)Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (SASRIN® linker), 4-(2,4-dimethoxyphenyl-hydroxymethyl)-phenoxy (Rink linker), 4-(4-hydroxymethyl-3-methoxphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the process of the invention can be advantageously carried out as described herein below but it will be immediately apparent to those skilled in the art how these procedures will have to be modified in case it is desired to synthesize one single compound of the above formula (I).

A number of reaction vessels (normally 24 to 192, typically 96) equal to the total number of compounds to be synthesized by the parallel method are loaded with 25 to 1000 mg, preferably 100 mg, of the appropriate functionalized solid support which is preferably derived from polystyrene cross-linked with 1 to 3% of divinylbenzene, or from Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e. g. 20% TFE/DCM, 35% THF/NMP) are beneficial for ensuring high reactivity and solvation of the resin-bound peptide chains (G. B. Fields and C. G. Fields, *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (SASRIN® linker, M. Mergler et al., *Tetrahedron Lett.* 1988, 29, 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the processes of the invention include the super acid labile 4-(2,4-dimethoxyphenyl-hydroxymethyl)-phenoxy linker (Rink linker, H. Rink, *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, A. Flörsheimer and B. Riniker, *Peptides* 1990, 1991, 131-133) which is also cleaved with 1% TFA/DCM in order to yield a peptide fragment containing all acid labile side-chain protective groups; and, in addition, the 2-chlorotritylchloride linker (K. Barlos et al., *Tetrahedron Lett.* 1989, 30, 3943-3946), which allows the peptide detachment using a mixture of glacial acetic acid/trifluoroethanol/DCM (1:2:7) for about 30 min.

Suitable protecting groups for amino acids and, respectively, for their residues are, for example, for the amino group (as is present e.g. also in the side-chain of lysine)
Cbz benzyloxycarbonyl
Boc tert.-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl
Trt triphenymethyl or trityl
ivDe 1-(4,4-dimethyl-2,6-dioxocyclohex-1-ylidene)-3-methylbutyl
for the carboxyl group (as is present e.g. also in the side-chain of aspartic and glutamic acid) by conversion into esters with the alcohol components
tBu tert.-butyl
Bn benzyl
Me methyl
Ph phenyl
Pac phenacyl
allyl
Tse trimethylsilylethyl
Tce trichloroethyl
Dmab 4-N-(1[4,4-dimethyl-2,6-dioxocyclohexylidene]-3-methylbutyl)-amino benzyl
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf 2,2,4,6,7-pentamethyldihydrobenzofuran-5-sulfonyl
for the hydroxy group (as is present e.g. in the side-chain of threonine and serine)
tBu tert.-butyl
Bn benzyl
Trt trityl
and for the mercapto group (as is present e.g. in the side-chain of cysteine)
Acm acetamidomethyl
tBu tert.-butyl
Bn benzyl
Trt trityl
Mtr 4-methoxytrityl.

The 9-fluorenylmethoxycarbonyl-(Fmoc)-protected amino acid derivatives are preferably used as the building blocks for the construction of the backbone-cyclized peptidomimetics of the invention. For the deprotection, i.e. cleaving off of the Fmoc group, 20% piperidine in DMF or 2% DBU/2% piperidine in DMF can be used.

The quantity of the reactant, i. e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The preferred workstations (without, however, being limited thereto) are Labsource's Combi-chem station, Protein Technologies' Symphony and MultiSyn Tech's Syro synthesizer, the latter additionally equipped with a transfer unit and a reservoir box during the process of detachment of the fully protected linear peptide from the solid support. All synthesizers are able to provide a controlled environment, for example, reactions can be accomplished at temperatures different from room temperature as well as under inert gas atmosphere, if desired.

Amide bond formation requires the activation of the α-carboxyl group for the acylation step. When this activation is being carried out by means of the commonly used carbodiimides such as dicyclohexylcarbodiimide (DCC, J. C. Sheehan and G. P. Hess, *J. Am. Chem. Soc.* 1955, 77, 1067-1068) or diisopropylcarbodiimide (DIC, D. Sarantakis et al., *Biochem. Biophys. Res. Commun.* 1976, 73, 336-342), the resulting dicyclo-hexylurea and diisopropylurea is insoluble and, respectively, soluble in the solvents generally used. In a variation of the carbodiimide method 1-hydroxybenzotriazole (HOBt, W. König and R. Geiger, *Chem. Ber.* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP, B. Castro et al., *Tetrahedron Lett.* 1975, 14, 1219-1222; B. Castro et al., *Synthesis* 1976, 751-752), or benzotriazol-1-yl-oxy-tris-pyrrolidino-phosphonium hexafluorophosphate (Py-BOP, J. Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, R. Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-azabenzotriazol-1-yl)-N,N,N',N'-tetramethyl-uronium tetrafluoroborate (TATU) or O-(7-aza-benzotriazol-1-yl)-N,N,N', N'-tetramethyl-uronium hexafluorophosphate (HATU)/7-aza-1-hydroxybenzotriazole (HOAt, L. A. Carpino et al., *Tetrahedron Lett*. 1994, 35, 2279-2282) or O-(6-Chloro-1H-benzotriazol-1-yl-)-N,N,N',N'-1,1,3,3-tetra-methyl-uronium tetrafluoro-borate (TCTU), or hexafluorophosphate (HCTU, O Marder, Y. Shvo and F. Albericio, HCTU and TCTU: New Coupling Reagents—Development and Industrial Applications, *Chimica Oggi* 2002, 20, 37-41) have also been used as coupling reagents as well as 1,1,3,3-bis(tetramethylene) chlorouronium hexafluorophosphate (PyClU, especially for coupling N-methylated amino acids, J. Coste et al., *Tetrahedron Lett*. 1991, 32, 1967) or pentafluorophenyl diphenylphosphinate (S. Chen and J. Xu, *Tetrahedron Lett*. 1991, 32, 6711).

Due to the fact that near-quantitative coupling reactions are essential, it is desirable to have experimental evidence for completion of the reactions. The ninhydrin test (E. Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (J. Meienhofer et al., *Int. J. Peptide Protein Res.* 1979, 13, 35-42).

The resin-bound intermediate within each reaction vessel is washed free of excess of retained reagents, of solvents, and of by-products by repetitive exposure to pure solvent(s).

Washing procedures are repeated up to about 30 times (preferably about 5 times), monitoring the efficiency of reagent, solvent, and by-product removal by methods such as TLC, GC, LC-MS or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Detachment of the fully protected linear peptide from the solid support is achieved by exposing the loaded resin with a solution of the reagent used for cleavage (preferably 3 to 5 mL). Temperature control, agitation, and reaction monitoring are implemented as described above. Via a transfer-unit the reaction vessels are connected with a reservoir box containing reservoir tubes to efficiently collect the cleaved product solutions. The resins remaining in the reaction vessels are then washed 2 to 5 times as above with 3 to 5 mL of an appropriate solvent to extract (wash out) as much of the detached products as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as $CH_2Cl_2$, DMF, dioxane, THF and the like. Various coupling reagents which were mentioned earlier as activators for the amide bond formation can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as $CH_2Cl_2$, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS, or 87.5% TFA, 2.5% DODT, 5% thioanisol, 5% $H_2O$ or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefore. The aqueous layer is collected and evaporated to dryness, and the fully deprotected cyclic peptide is obtained. Alternatively the deprotected cyclic peptide can be precipitated and washed using cold $Et_2O$.

Depending on its purity, this peptide derivative can be used directly for biological assays, or it has to be further purified, for example by preparative HPLC.

As mentioned earlier, it is thereafter possible, if desired, to convert a fully deprotected product of formula (I) thus obtained into a pharmaceutically acceptable salt or to convert a pharmaceutically acceptable, or unacceptable, salt thus obtained into the corresponding free compound of formula (I) or into a different, pharmaceutically acceptable, salt. Any of these operations can be carried out by methods well known in the art.

In general the building blocks for the peptidomimetics of the present invention can be synthesized according to the literature methods, which are known to a person skilled in the art or are commercially available. All other corresponding amino acids have been described either as unprotected or as Boc- or Fmoc-protected racemates, (D)- or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of α-amino acids include: R. Duthaler, *Tetrahedron* (Report) 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, I. A. Yamskov, *Russian Chem. Rev.* 1991, 60, 1163-1179; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989, Chapter 7, p. 257-279). Kinetic resolution using hydrolytic enzymes involves hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron Report* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989).

The backbone-cyclized peptidomimetics of the invention can be used in a wide range of applications in order to modulate GLP-1 receptor activity leading to the desired therapeutic effect in man or, due to their similar etiology, in other mammals. Especially, they can be used as agents for treating and/or preventing and/or delaying the onset of diseases, disorders or conditions in the disease areas of diabetes, such as type 2 diabetes and type 1 diabetes; or prediabetes, such as impaired glucose tolerance; or diabetes-related complications and comorbidities, such as diabetic retinopathy, diabetic neuropathy, diabetic nephropathy, impaired wound healing, dyslipidemia, and vascular diseases and obesity; or hyperglycemia; or metabolic syndrome; or hypertension; or insulin resistance; or obesity; or cognitive disorders, such as cognitive deficits; or mood disorders; or neurodegenerative diseases, such as Alzheimer's disease; or traumatic brain injuries; or stroke; or insufficient satiety; or cardiovascular disorders and diseases, such as coronary heart disease and myocardial infarction; or atherosclerosis; or gastric ulcers; or inflammatory bowel syndrome. They can be administered singly, as mixtures of several backbone-cyclized peptidomimetics of the invention, in combination with at least one therapeutic active substance selected from the group consisting of antidiabetic agents, agents for the prevention and/or treatment of complications or comorbidities associated or resulting from diabetes, antihypertensive agents, antiobesity agents, anti-atherosclerotic agents, or agents for appetite regulation, or in combination with other pharmaceutically active agents. The backbone-cyclized peptidomimetics can be administered per se or as pharmaceutical compositions.

The active ingredient(s) consisting of, or containing the backbone-cyclized peptidemimetics of the invention may be administered per se or applied as a pharmaceutical preparation, e.g. an appropriate formulation together with carriers, diluents or excipients well known in the art.

Pharmaceutical compositions comprising backbone-cyclized peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active backbone-cyclized peptidomimetics into preparations which can be used pharmaceutically. Proper formulation depends upon the method of administration chosen.

For topical administration the backbone-cyclized peptidomimetics of the invention may be formulated, but not limited to, as solutions, gels, ointments, creams, suspensions, as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the backbone-cyclized peptidomimetics of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the backbone-cyclized peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds of the invention can be readily formulated by combining the active backbone-cyclized peptidomimetics with pharmaceutically acceptable carriers well known in the art. Such carriers enable the backbone-cyclized peptidomimetics of the invention to be formulated, but not limited to, as tablets, pills, dragees, capsules, liquids, gels, syrups, slurries, suspensions, for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, disintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, but not limited to, suspensions, elixirs and solutions, suitable carriers, excipients or diluents include water, glycols, oils, alcohols. In addition, flavoring agents, preservatives, coloring agents and the like may be added.

For buccal administration, the composition may take the form, but not limited to, of tablets, lozenges, formulated as well known in the art.

For administration by inhalation, the backbone-cyclized peptidomimetics of the invention are conveniently delivered in form of an aerosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the backbone-cyclized peptidomimetics of the invention and a suitable powder base such as lactose or starch.

The compounds may also be formulated in rectal or vaginal compositions such as solutions for enema or suppositories together with appropriate suppository bases such as cocoa butter or other glycerides.

In addition to the formulations described above, the backbone-cyclized peptidomimetics of the invention may also be formulated as depot preparations. Such long acting formulations may be administered by implantation (e.g. subcutaneously or intramuscularly) or by intramuscular injection. For the manufacture of such depot preparations the backbone-cyclized peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the backbone-cyclized peptidomimetics of the invention may be delivered using a sustained-release system, such as semipermeable matrices of solid polymers containing the therapeutic agent (e.g. for coated stents). Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the backbone-cyclized peptidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free base forms.

In addition, the compounds of the present invention and their pharmaceutical acceptable salts may be used per se or in any appropriate formulation in morphological different solid state forms, which may or may not contain different amounts of solvent, e.g. hydrate.

The backbone-cyclized peptidomimetics of the invention, or compositions thereof, will generally be used in an amount effective to achieve the intended purpose. It is to be understood that the amount used will depend on a particular application.

For the use of treating or preventing diseases, disorders, or conditions with an etiology comprising, or associated with the GLP-1 receptor, the backbone-cyclized peptidomimetics of the invention or compositions thereof, are administered or applied in a therapeutically effective amount. Determination of a therapeutically effective amount is well within the capacities of those skilled in the art, especially in view of the detailed disclosure provided herein.

For systemic administration, a therapeutically effective dose can be estimated initially from in vitro assays. For example, a dose can be formulated in animal models to achieve a circulating backbone-cyclized peptidomimetic concentration range that includes the $EC_{50}$ as determined in a cell-based assay. Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as agents for GLP-1R modulation may be adjusted individually to provide plasma levels of the backbone-cyclized peptidomimetics of the invention which are sufficient to maintain the therapeutic effect. Therapeutically effective serum levels may be achieved by administering multiple doses each day.

In cases of local administration or selective uptake, the effective local concentration of the backbone-cyclized peptidomimetics of the invention may not be related to plasma concentration. One having the ordinary skill in the art will be able to optimize therapeutically effective local dosages without undue experimentation.

The amount of backbone-cyclized peptidomimetics of the invention administered will, of course, be dependent on the subject being treated, on the subject's weight, the severity of the affliction, the manner of administration and the judgement of the prescribing physician.

Normally, a therapeutically effective dose of the backbone-cyclized peptidomimetics of the invention described herein will provide therapeutic benefit without causing substantial toxicity.

Toxicity of the backbone-cyclized peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the backbone-cyclized peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. E. Fingl et al. 1975, In: *The Pharmacological Basis of Therapeutics*, Ch. 1, p. 1).

The effective dosage of the active ingredients employed may vary depending on the particular compound or pharmaceutical preparation employed, the mode of administration and the severity and type of the condition treated. Thus, the dosage regimen is selected in accordance with factors including the route of administration and the clearance pathway, e.g. the renal and hepatic function of the patient. A physician, clinician or veterinarian skilled in the art can readily determine and prescribe the amount of the single active ingredients required to prevent, ameliorate or arrest the progress of the condition or disease. Optimal precision in achieving concentration of active ingredients without toxicity requires a regimen based on the kinetics of the active ingredients' availability to the target sites. This involves a consideration of the distribution, equilibrium, and elimination of the active ingredients.

The following Examples illustrate the present invention but are not to be construed as limiting its scope in any way.

ABBREVIATIONS

Ac Acetyl;
AcOH Acetic acid;
BSA Bovine serum albumin;
Boc tert-Butyloxycarbonyl;
DIPEA Diisopropylethylamine;
DMF N,N-Dimethylformamide;
DODT 3,6-Dioxa-1,8-octanedithiol;
$Et_2O$ Diethylether;
eq. Equivalent;
Fmoc Fluorenylmethyloxycarbonyl;
HATU O-(7-Aza-benzotriazole-1-yl)-N,N,N',N'-tetramethyluronium hexafluorophosphate;
HBTU O-(Benzotriazol-1-yl)-N,N,N',N'-tetramethyluronium hexafluorophosphate;
HCTU O-(6-Chlorobenzotriazol-1-yl)-N,N,N',N'-tetramethyluronium hexafluorophosphate;
HEPES 4-(2-Hydroxyethyl)-1-piperazineethanesulfonic acid;
HOAt 1-Hydroxy-7-azabenzotriazole;
IBMX 3-lsobutyl-1-nnethylxanthine;
MeOH Methanol;
MTP Microtiter plate;
NMP 1-Methyl-2-pyrrolidinone;
PyBop® (Benzotriazol-1-yloxy)tripyrrolidinophosphonium hexafluorophosphate;
TFA Trifluoroacetic acid;
TIS Triisopropylsilane;
rt Room temperature.

EXAMPLES

1. Peptide Synthesis
1.1 General Synthetic Procedures

A general method for the synthesis of the peptidomimetics of the present invention is exemplified in the following. This is to demonstrate the principal concept and does not limit or restrict the present invention in any way. A person skilled in the art is easily able to modify these procedures, especially, but not limited to, choosing a different starting position within the ring system, to still achieve the preparation of the claimed cyclic peptidomimetic compounds of the present invention.

Coupling of the First Protected Amino Acid Residue to the Resin

In a dried flask, 2-chlorotritylchloride resin (polystyrene, 1% crosslinked; loading: 1.4 mmol/g) was swollen in dry $CH_2Cl_2$ for 30 min (7 ml $CH_2Cl_2$ per g resin). A solution of 0.8 eq of the Fmoc-protected amino acid and 6 eq of DIPEA in dry $CH_2Cl_2$/DMF (4/1, v/v) (10 ml per g resin) was added. After shaking for 2-4 h at rt the resin was filtered off and washed successively with $CH_2Cl_2$, DMF, $CH_2Cl_2$, DMF and $CH_2Cl_2$. Then a solution of dry $CH_2Cl_2$/MeOH/DIPEA (17:2:1, v/v/v) was added (10 ml per g resin). After shaking for 3×30 min the resin was filtered off in a pre-weighed sinter funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin was dried under high vacuum overnight. The final mass of resin was calculated before the qualitative control.

The following preloaded resins were prepared: Fmoc-Ala-2-chlorotrityl resin and Fmoc-Leu-2-chlorotrityl resin.

Synthesis of the Fully Protected Peptide Fragment

The synthesis was carried out on a Syro-peptide synthesizer (MultiSynTech GmbH) using 24 to 96 reaction vessels. In each vessel were placed approximately 80 mg of the above resin (weight of the resin before loading). The following reaction cycles were programmed and carried out:

| Step | Reagent | Time |
|---|---|---|
| 1 | $CH_2Cl_2$, wash and swell (manual) | 1 × 3 min |
| 2 | DMF, wash and swell | 2 × 30 min |
| 3 | 20% piperidine/DMF | 1 × 5 min and 1 × 15 min |
| 4 | DMF, wash | 5 × 1 min |
| 5 | 3.5 eq. Fmoc amino acid/3.5 eq. HOAt in DMF or NMP + 3.5 eq. PyBOP/7 eq DIPEA or 3.5 eq. DIC | 1 × 40 min |
| 6 | 3.5 eq. Fmoc amino acid/3.5 eq. HOAt in DMF or NMP + 3.5 eq. HATU or PyBOP or HCTU + 7 eq. DIPEA | 1 × 40 min |
| 7 | DMF, wash | 5 × 1 min |
| 8 | 20% piperidine/DMF | 1 × 5 min and 1 × 15 min |
| 9 | DMF, wash | 5 × 1 min |
| 10 | $CH_2Cl_2$, wash (at the end of the synthesis) | 3 × 1 min |

Steps 5 to 9 are repeated to add each amino-acid residue.

After the synthesis of the fully protected peptide fragment had been terminated, the cleavage, cyclization and work up procedures, as described herein below, were used for the preparation of the final compounds.

Cleavage, Backbone Cyclization and Deprotection of the Peptide

After assembly of the linear peptide, the resin was suspended in 1 ml of 1% TFA in $CH_2Cl_2$ (v/v; 0.14 mmol) for 3 minutes and filtered, and the filtrate was neutralized with 1 ml of 20% DIPEA in $CH_2Cl_2$ (v/v; 1.15 mmol). This procedure was repeated four times to ensure completion of the cleavage. The resin was washed three times with 1 ml of $CH_2Cl_2$. The $CH_2Cl_2$ layers containing product were evaporated to dryness.

The fully protected linear peptide was solubilised in 8 ml of dry DMF. Then 2 eq. of HATU and 2. eq. of HOAt in dry DMF (1-2 ml) and 4 eq. of DIPEA in dry DMF (1-2 ml) were added to the peptide, followed by stirring for ca. 16 h. The volatiles were removed by evaporation. The crude cyclic peptide was dissolved in 7 ml of $CH_2Cl_2$ and washed three times with 4.5 ml 10% acetonitrile in water (v/v). The $CH_2Cl_2$ layer was then evaporated to dryness.

To fully deprotect the peptide, 4-7 ml of cleavage cocktail TFA/TIS/$H_2O$ (95:2.5:2.5, v/v/v) was added, and the mixture was kept for 2.5-4 h at room temperature until the reaction was completed. The reaction mixture was evaporated close to dryness and the peptide precipitated with 7 mL of cold $Et_2O$/pentane (1:1, v/v). The precipitate was washed three times with 3 mL of cold $Et_2O$/pentane (1:1, v/v), and was subsequently purified by preparative reverse phase LC-MS.

After lyophilisation the products were obtained typically as white to off-white powders and analysed by HPLC-ESI-MS methods as described below. Analytical data after preparative HPLC purification are shown in Table 1.

1.2 Analytical Methods

Analytical Method A:

Analytical HPLC retention times (RT, in minutes) were determined using an Ascentis Express C18 column (50×2.1 mm, 2.7 μm) with the following solvents A ($H_2O$+0.1% TFA) and B ($CH_3CN$+0.085% TFA) and the gradient: 0-0.05 min: 97% A, 3% B; 3.3 min: 15% A, 85% B; 3.32 min: 3% A, 97% B; 3.32-3.55 min: 3% A, 97% B; 3.57-3.7 min: 97% A, 3% B. Flow rate=1.6 ml/min at 55° C.

Analytical Method B:

Analytical HPLC retention times (RT, in minutes) were determined using an Ascentis Express C18 column (50×3 mm, 2.7 μm) with the following solvents A ($H_2O$+0.1% TFA) and B ($CH_3CN$+0.085% TFA) and the gradient: 0-0.05 min: 97% A, 3% B; 4.95 min: 3% A, 97% B; 4.95-5.35 min: 3% A, 97% B; 5.37-5.4 min: 97% A, 3% B. Flow rate=1.3 ml/min at 55° C. Analytical Method C:

Analytical HPLC retention times (RT, in minutes) were determined using an Ascentis Express C8 column (100×3 mm, 2.7 μm) with the following solvents A ($H_2O$+0.1% TFA) and B ($CH_3CN$+0.085% TFA) and the gradient: 0-0.1 min: 95% A, 5% B; 7.0 min: 15% A, 85% B; 7.02 min: 3% A, 97% B; 7.02-7.5 min: 3% A, 97% B; 7.52-7.8 min: 95% A, 5% B. Flow rate=1.4 ml/min at 55° C.

Analytical Method D:

Analytical HPLC retention times (RT, in minutes) were determined using an Ascentis Express C8 column (100×3 mm, 2.7 μm) with the following solvents A ($H_2O$+0.1% TFA) and B ($CH_3CN$+0.085% TFA) and the gradient: 0-0.1 min: 95% A, 5% B; 11.0 min: 15% A, 85% B; 11.02 min: 3% A, 97% B; 11.02-12.5 min: 3% A, 97% B; 12.55-13.5 min: 95% A, 5% B. Flow rate=0.750 ml/min at 55° C.

1.3 Synthesis of Peptide Sequences

Examples 1 to 42 and 44 to 54 Shown in Table 1

The peptides were synthesized according the general method starting with the amino acid L-Ala which was grafted to the resin (Fmoc-Ala-2-chlorotrityl resin). The linear peptides were synthesized on the solid support according to the procedure described above in the following sequence: Resin-Ala-$P^4$-$P^3$-$P^2$-$P^1$-$T^2$-$T^1$-$P^8$-$P^7$-$P^6$. The products were cleaved from the resin, cyclized, deprotected and purified by preparative reverse phase LC-MS as described above.

After lyophilisation the products were obtained as white to off-white powders and characterised by HPLC-MS, analytical method A, B, or C as described above. For analytical data, see Ex. 1. to 42 and 44 to 54 in Table 1.

Example 43 is Shown in Table 1

The peptide was synthesized according to the general method starting with the amino acid L-Leu which was grafted to the resin (Fmoc-Leu-2-chlorotrityl resin). The linear peptide was synthesized on the solid support according to the procedure described above in the following sequence: Resin-Leu-$P^3$-$P^2$-$P^1$-$T^2$-$T^1$-$P^8$-$P^7$-$P^6$-$P^5$. The product was cleaved from the resin, cyclized, deprotected and purified by preparative reverse phase LC-MS as described above.

After lyophilisation the product was obtained as white to off-white powder and characterised by HPLC-MS, analytical method B as described above. For analytical data, see Ex. 43 in Table 1.

1.4 Sequence Data

2. Biological Methods 2.1 Preparation of the Peptide Samples

Lyophilized peptides were weighed on a Microbalance (Mettler MX5) and dissolved in aqueous 90% DMSO to a final concentration of 10 mM unless otherwise stated. Stock solutions were kept at +4° C., and protected from light.

2.2 Human GLP-1 Receptor Cell-Based Assay

CHO chAMPion cells (Axxam SpA; S. Corazza, *Assay Drug Dev. Technol.* 2009, 7, 304-307) stably co-expressing the human glucagon-like peptide-1 receptor (GLP-1R), the $Ca^{2+}$-sensitive photoprotein PHOTINA® (S. Bovolenta et al., *J. Biomol. Screen.* 2007, 12, 694-704) and a mutated

TABLE 1

Examples (Ex.)

| Ex. | $P^{1a)}$ | $P^{2a)}$ | $P^{3a)}$ | $P^{4a)}$ | $P^{5a)}$ | $P^{6a)}$ | $P^{7a)}$ | $P^{8a)}$ | $T^{1a)}$ | $T^{2a)}$ | Analyt. Meth. | $MS^{b)}$ | RT [min] | Purity [%] |
|---|---|---|---|---|---|---|---|---|---|---|---|---|---|---|
| 1 | Phe | Phe | Gln | Tyr | Ala | Trp | Glu | Tyr | $^D$Pro | Chx | A | 1357.7 | 1.80 | 94 |
| 2 | Phe | 3Pal | Gln | Tyr | Ala | Trp | Glu | Tyr | $^D$Pro | Chx | A | 680.0 | 1.49 | 95 |
| 3 | Phe | Phe(4NH$_2$) | Gln | Tyr | Ala | Trp | Glu | Tyr | $^D$Pro | Chx | A | 687.0 | 1.51 | 95 |
| 4 | Phe | His(Bn) | Gln | Tyr | Ala | Trp | Glu | Tyr | $^D$Pro | Chx | A | 719.5 | 1.68 | 95 |
| 5 | Phe | Tyr(Bn) | Gln | Tyr | Ala | Trp | Glu | Tyr | $^D$Pro | Chx | A | 732.5 | 2.08 | 92 |
| 6 | Phe | Tyr(Ph) | Gln | Tyr | Ala | Trp | Glu | Arg | $^D$Pro | Chx | A | 722.0 | 1.82 | 95 |
| 7 | Phe | Tyr(Ph) | Gln | Tyr | Ala | Trp | Glu | Tyr | $^D$Pro | Chx | A | 1449.5 | 2.06 | 87 |
| 8 | Phe | Trp | Gln | Tyr(Me) | Ala | Trp | Glu | Tyr | $^D$Pro | Chx | A | 1410.7 | 1.93 | 85 |
| 9 | Phe | Trp | Gln | Tyr | Ala | Trp | Glu | Tyr(Me) | $^D$Pro | Chx | A | 1410.7 | 2.03 | 92 |
| 10 | Phe | Phe | Gln | Tyr | Ala | Trp | Glu | Arg | $^D$Pro | Chx | A | 676.0 | 1.55 | 95 |
| 11 | Phe | Tyr(Ph) | Gln | Tyr | Ala | Trp | Glu | Arg | $^D$Pro | Aib | A | 702.0 | 1.68 | 95 |
| 12 | Phe | Trp | Leu | Tyr | Ala | Trp | Glu | Tyr | $^D$Pro | Chx | A | 1381.6 | 2.15 | 86 |
| 13 | Phe | Glu | Leu | Tyr | Ala | Trp | Glu | Tyr | $^D$Pro | Ind | C | 1358.3 | 4.31 | 93 |
| 14 | Phe | Tyr | Gln | Tyr | Ala | Trp | Glu | Tyr | $^D$Pro | Chx | A | 687.5 | 1.64 | 95 |
| 15 | Phe | Trp | Gln | Tyr | Ala | Trp | Glu | His(Bn) | $^D$Pro | Chx | C | 731.0 | 3.85 | 89 |
| 16 | Phe | Glu | Leu | Tyr | Ala | Trp | Glu | Trp | $^D$Pro | Chx | A | 1347.6 | 2.15 | 90 |
| 17 | Phe | Trp | Gln | Tyr | Ala | Trp | Glu | Trp | $^D$Pro | Chx | A | 1419.7 | 1.99 | 89 |
| 18 | Phe | Trp | Gln | Tyr | Ala | Trp | Glu | Trp(5OH) | $^D$Pro | Chx | C | 718.4 | 3.84 | 88 |
| 19 | Phe | 3Pal | Gln | Tyr | Ala | Trp | Glu | Arg | $^D$Pro | Chx | A | 676.5 | 1.22 | 95 |
| 20 | Phe | His | Leu | Tyr | Ala | Trp | Glu | Tyr | $^D$Pro | Chx | A | 667.0 | 1.81 | 95 |
| 21 | Phe | Phe(4NH$_2$) | Gln | Tyr | Ala | Trp | Glu | Arg | $^D$Pro | Chx | A | 683.5 | 1.26 | 95 |
| 22 | Phe | Trp | Gln | Tyr | Ala | Trp | Glu | Tyr(Bn) | $^D$Pro | Chx | A | 1486.6 | 2.32 | 95 |
| 23 | Phe | Trp | Gln | Tyr(Me) | Ala | Trp | Glu | Arg | $^D$Pro | Chx | A | 702.7 | 1.69 | 95 |
| 24 | Phe | Trp | Gln | Tyr | Ala | Trp | Glu | Phe | $^D$Pro | Chx | A | 1380.7 | 2.06 | 95 |
| 25 | Phe | Glu | Leu | Tyr | Ala | Trp | Glu | Trp(5OH) | $^D$Pro | Chx | A | 682.5 | 1.92 | 95 |
| 26 | Phe | Glu | Leu | Leu | Ala | Trp | Glu | Phe | $^D$Pro | Dpg | C | 1274.5 | 5.99 | 95 |
| 27 | Phe | Trp | Gln | Phe | Ala | Trp | Glu | Tyr | $^D$Pro | Chx | A | 1380.6 | 1.93 | 95 |
| 28 | Phe | Glu | Leu | Tyr | Ala | Trp | Trp(5OH) | Tyr | $^D$Pro | Chx | A | 1397.6 | 2.08 | 95 |
| 29 | Phe | Glu | Leu | Tyr(Me) | Ala | Trp | Glu | Tyr | $^D$Pro | Chx | A | 670.1 | 2.23 | 95 |
| 30 | Phe | Trp | Gln | Tyr | Ala | Trp | Glu | Phe(4NH$_2$) | $^D$Pro | Chx | A | 698.5 | 1.55 | 95 |
| 31 | Phe | Glu | Leu | Tyr | Ala | Trp | Glu | Phe | $^D$Pro | Chx | A | 1308.4 | 2.23 | 95 |
| 32 | Phe | Tyr(Me) | Gln | Tyr | Ala | Trp | Glu | Tyr | $^D$Pro | Chx | A | 1387.5 | 1.80 | 95 |
| 33 | Phe | 4Pal | Gln | Tyr | Ala | Trp | Glu | Tyr | $^D$Pro | Chx | A | 680.0 | 1.47 | 95 |
| 34 | Phe | Glu | Leu | Tyr(Me) | Ala | Trp | Glu | Tyr(Me) | $^D$Pro | Chx | C | 1352.3 | 5.35 | 95 |
| 35 | Phe | Trp(5OH) | Gln | Tyr | Ala | Trp | Glu | Tyr | $^D$Pro | Chx | A | 1412.5 | 1.69 | 90 |
| 36 | Phe | Glu | Leu | Tyr | Ala | Trp | Glu | His(Bn) | $^D$Pro | Chx | A | 695.0 | 1.84 | 95 |
| 37 | Phe | Glu | Leu | Phe(4CN) | Ala | Trp | Glu | Tyr | $^D$Pro | Chx | C | 1333.3 | 4.70 | 95 |
| 38 | Phe | Glu | Leu | Tyr | Ala | Trp | Cit | Tyr | $^D$Pro | Chx | A | 677.0 | 1.92 | 95 |
| 39 | Phe | Glu | Leu | Tyr | Ala | Trp | Glu | His | $^D$Pro | Chx | A | 650.0 | 1.64 | 95 |
| 40 | Phe | Gln | Leu | Tyr | Ala | Trp | Glu | Tyr | $^D$Pro | Chx | A | 1323.7 | 1.94 | 95 |
| 41 | Phe | Glu | Leu | Tyr | Ala | Trp | Glu | 3Pal | $^D$Pro | Chx | D | 655.3 | 6.07 | 95 |
| 42 | Phe | Glu | Leu | Tyr | Ala | Trp | Glu | Arg | $^D$Pro | Chx | D | 659.4 | 6.04 | 95 |
| 43 | Phe | Glu | Leu | Leu | Ala | Trp | Glu | Phe | $^D$Pro | Chx | B | 1258.7 | 3.64 | 95 |
| 44 | Phe | Glu | Leu | Leu | Ala | Trp | Glu | Phe | $^D$Pro | Cyp | B | 622.9 | 3.58 | 95 |
| 45 | Phe | Glu | Leu | Leu | Ala | Trp | Glu | Phe | $^D$Pro | Aib | A | 1218.6 | 2.37 | 95 |
| 46 | Phe | Trp | Gln | Leu | Ala | Trp | Glu | Phe | $^D$Pro | Cyp | B | 658.9 | 3.08 | 86 |
| 47 | Phe | Glu | Leu | Leu | Ala | Trp | Glu | Phe | $^D$Pro | Deg | B | 1246.6 | 3.65 | 95 |
| 48 | Phe | Glu | Leu | Tyr | Ala | Trp | Glu | Phe | $^D$Pro | Cyp | B | 648.0 | 3.12 | 95 |
| 49 | Phe | Gln | Leu | Tyr | Ala | Trp | Hgl | Tyr | $^D$Pro | Chx | B | 1337.7 | 2.82 | 89 |
| 50 | Phe | Glu | Leu | Tyr | Ala | Trp | Glu | Phg | $^D$Pro | Chx | B | 1294.7 | 3.08 | 95 |
| 51 | Phe | His | Leu | Tyr | Ala | Trp | Glu | Tyr | $^D$Pro | Aib | A | 646.4 | 1.73 | 95 |
| 52 | Phe | Glu | Leu | Leu | Ala | Trp | Glu | Phe | $^D$Pro | Ind | B | 1292.7 | 3.61 | 89 |
| 53 | Phe | Glu | Leu | Leu | Ala | Trp | Glu | Phe | $^D$Pro | Ac7c | B | 1272.6 | 3.77 | 95 |
| 54 | Phe | Glu | Leu | Leu | Ala | Trp | Glu | Phe | $^D$Pro | Ac8c | B | 1286.6 | 3.87 | 95 |

$^{a)}$Abbreviations of amino acid see listing above.
$^{b)}$MS: m/z for either $[M + 1H]^{1+}$ or $[M + 2H]^{2+}$.

cAMP-activated calcium ion channel (WO2004/083803 A2) were used to monitor GLP-1R signaling after stimulation with an agonist. Activation of the Gas-coupled GPCR GLP-1R was monitored by measuring the flash luminescence of the $Ca^{2+}$-sensitive photoprotein as reporter system with FLIPR$^{TETRA}$ screening instrumentation (Molecular Devices) upgraded with an ICCD Camera (MDC). For data quality check and data analysis the Genedata SCREENER® software was used.

The reference agonist GLP-1 (glucagon-like peptide-1 amide fragment 7-36) and forskolin were purchased from Sigma (cat. G8147 and F6886, respectively) and prepared according to each ligand's specifications. All handling of ligands were done to ensure proper control throughout the experiments. The steps of the implemented workflow and data analysis are mainly as follows:

Assay Plate Seeding:

Stably transfected chAMPion cells are seeded 10000 c/w in 384 MTP in Dulbecco's MEM/nutrient mix F12 (Bio-Whittaker cat. BE04-687F/U1; 500 mL) supplemented with sodium pyruvate (BioWhittaker cat. BE13-115E; 5 mL of 100 mM solution), HEPES (BioWhittaker cat. BE17-737E; 6.5 mL of 1M solution), sodium bicarbonate (BioWhittaker cat. BE17-613E; 25 mL of 7.5% solution), fetal bovine serum (Euroclone cat. ECS 0180L; 50 mL), penicillin-streptomycin (BioWhittaker cat. DE17-602E; 5 mL of 100× solution), 1 mg/mL G418 (selection antibiotic for GLP-1R) and 200 µg/mL hygromycin in 25 µL/well for 24 hours. On the day of the experiment, plates are removed from the incubator, freed from the growth medium, equilibrated at room temperature for 1 h, loaded with 30 µl/well of $Ca^{2+}$ free Tyrode's buffer containing 20 µM coelentrazine and 500 µM IBMX, and incubated for 4 hours at room temperature.

Assay:

All compounds were tested at 8 concentrations, starting from 50 µM in quadruplicate, intra-plate (dilution step 1:2.15) to determine $EC_{50}$ values. After incubation, the volume in all the wells is flattened to 20 αL by aspiration with a CYBIO®-VARIO pipettor. First Injection (10 µL of test compounds in $Ca^{2+}$ free Tyrode's buffer, DMSO 0.5% v/v and BSA 0.01%; or 10 µL of reference compounds GLP-1 or forskolin in Ca' free Tyrode's buffer, DMSO 0.5% v/v and BSA 0.01%) is performed by the FLIPR$^{TETRA}$ and the kinetic response is optionally monitored over a period of 60 seconds. Incubation for 30 minutes at room temperature is followed by the Second Injection (Tyrode's buffer+10 mM $CaCl_2$)) and the kinetic response is monitored over a period of 60 seconds.

Data Analysis and Results:

The kinetic response is divided into two distinct phases: monitoring the kinetic response after the First Injection, termed Compound Addition (CA), and monitoring the kinetic response after the Second Injection of 10 mM $CaCl_2$, termed Target Activation (TA). Agonist activity of compounds is evaluated in the Target Activation (TA) phase and it is based on normalization to TA activation by forskolin at 10 µM or GLP-1 at 3.16 nM ($EC_{100}$)

A good correlation was observed between $EC_{50}$, data normalized by forskolin and by GLP-1. The results of the GLP-1R assays based on normalization by forskolin are summarized in Table 2.

2.3 Results

TABLE 2

Glucagon-like peptide-1 (GLP-1) receptor assay

| Ex. | $EC_{50}$ (µM) Target Activation (TA) |
|---|---|
| 1 | 0.09 ± 0.05 |
| 2 | 0.28 ± 0.26 |
| 3 | 0.18 ± 0.18 |
| 4 | 0.09 ± 0.02 |
| 5 | 0.15 ± 0.05 |
| 6 | 0.19 ± 0.12 |
| 7 | 0.57 ± 0.58 |
| 8 | 0.35 ± 0.30 |
| 9 | 0.80 ± 0.69 |
| 10 | 0.39 ± 0.23 |
| 11 | 0.54 ± 0.43 |
| 12 | 0.48 ± 0.24 |
| 13 | 0.66 ± 0.25 |
| 14 | 0.72 ± 0.43 |
| 15 | 0.70 ± 0.42 |
| 16[a] | 0.41 |
| 17 | 0.60 ± 0.29 |
| 18 | 0.82 ± 0.55 |
| 19 | 0.72 ± 0.38 |
| 20 | 0.59 ± 0.35 |
| 21 | 0.67 ± 0.28 |
| 22 | 0.72 ± 0.40 |
| 23 | 0.67 ± 0.22 |
| 24 | 0.89 ± 0.51 |
| 25 | 0.94 ± 0.68 |
| 26 | 1.0 ± 0.5 |
| 27[a] | 0.58 |
| 28 | 1.2 ± 0.9 |
| 29[a] | 0.62 |
| 30[a] | 0.63 |
| 31[a] | 0.68 |
| 32 | 0.92 ± 0.31 |
| 33 | 0.99 ± 0.37 |
| 34[a] | 0.73 |
| 35 | 1.1 ± 0.5 |
| 36[a] | 0.85 |
| 37[a] | 0.88 |
| 38[a] | 0.93 |
| 39 | 1.0 ± 0.1 |
| 40 | 1.2 ± 0.6 |
| 41 | 0.83 ± 0.60 |
| 42 | 2.2 ± 1.0 |
| 43 | 4.5 ± 2.6 |
| 44 | 2.9 ± 0.7 |
| 45[a] | 1.8 |
| 46 | 5.1 ± 1.4 |
| 47[a] | 2.0 |
| 48 | 0.90 ± 0.18 |
| 49[a] | 3.1 |
| 50[a] | 2.4 |
| 51[a] | 3.3 |
| 52 | 0.82 ± 0.25 |
| 53[a] | 2.1 |
| 54[a] | 1.1 |

[a]Values obtained from single experiment

The invention claimed is:

1. A compound of the general formula (I)

cyclo[-P$^1$-P$^2$-P$^3$-P$^4$-P$^5$-P$^6$-P$^7$-P$^8$-T$^1$-T$^2$-]     (I)

wherein the single elements T or P are connected in either direction from the carbonyl (C=O) point of attachment to the nitrogen (N) of the next element and wherein T$^1$ is a D α-amino acid residue selected from the group consisting of

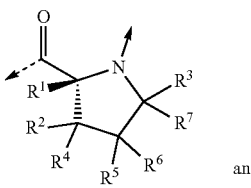
(AA1)

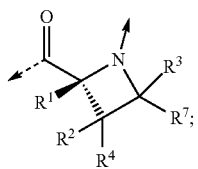
(AA2)

$T^2$ is an L or D α-amino acid residue selected from the group consisting of

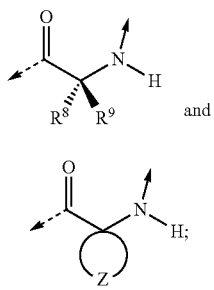
(AA3)

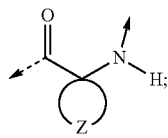
(AA4)

$P^1$ is Phe; Tyr; 3Pal; 2Thi; or 3Thi;

$P^2$ is Asp; Asn; Glu; Hgl; Gln; hGln; Cit; or an L α-amino acid residue of formula

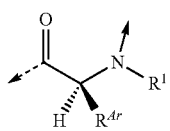
AA5

$P^3$ is Leu; Nle; Cha; Chg; Asn; Gln; hGln; or Cit;

$P^4$ is Leu; Nle; Val; or an L α-amino acid residue of formula

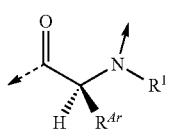
AA5

$P^5$ is Ala; Aib; or Abu;

$P^6$ is Trp; Trp(5OH); Tpi; or Trp(1Me);

$P^7$ is Asp; Asn; Glu; Hgl; Gln; hGln; or Cit;

$P^8$ is Arg; hArg; Agp; Lys; hLys; Orn; or an L α-amino acid residue of formula

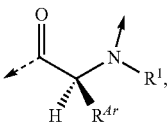
AA5 with the proviso that if $P^3$ is Asn; Gln; hGln; or Cit; then
  $P^2$ is an L α-amino acid residue of formula AA5;
  $P^7$ is Asp; Glu; Hgl; or Cit;

or if $P^3$ is Leu; Nle; Cha; or Chg; and $P^2$ is Asn; Gln; hGln; Cit; or an L α-amino acid residue of formula AA5; then
  $P^7$ is Glu; or Hgl;

$R^{Ar}$ is, with the proviso of containing less than 26 carbon- and/or heteroatoms, $-(CR^{20}R^{22})_nR^{27}$; $-(CH_2)_nO(CH_2)_mR^{27}$; $-(CH_2)_nS(CH_2)_mR^{27}$; or $-(CH_2)_nNR^{25}(CH_2)_mR^{27}$;

$R^1$, $R^2$ and $R^3$ are independently
  H; $CF_3$; or $CH_3$;

$R^4$, $R^5$ and $R^6$ are independently
  H; F; $CF_3$; $C_{1-8}$-alkyl; $C_{2-8}$-alkenyl; $C_{2-8}$-alkynyl; cycloalkyl; heterocycloalkyl; $-(CHR^{12})_oOR^{15}$; $-O(CO)R^{15}$; $-(CHR^{12})_oSR^{15}$; $-(CHR^{12})_oNR^{15}R^{16}$; $-(CHR^{12})_oOCONR^{15}R^{16}$; $-(CHR^{12})_oNR^1CONR^{15}R^{16}$; $-(CHR^{12})_oNR^1COOR^{15}$; $-(CHR^{12})_oNR^1COR^{15}$; $-(CHR^{12})_oCOOR^{15}$; $-(CHR^{12})_oCONR^{15}R^{16}$; $-(CHR^{12})_oPO(OR^1)_2$; $-(CHR^{12})_oSO_2R^{15}$; $-(CHR^{12})_oNR^1SO_2R^{15}$; or $-(CHR^{12})_oSO_2NR^{15}R^{16}$;

$R^4$ and $R^2$; or $R^5$ and $R^6$ taken together can form:
  $=O$; or $-(CHR^1)_p-$;

$R^4$ and $R^5$; or $R^6$ and $R^7$ taken together can form:
  $-(CHR^1)_p-$; $-(CH_2)_tO(CH_2)_u-$; $-(CH_2)_tS(CH_2)_u-$; or $-(CH_2)_tNR^1(CH_2)_u-$;

$R^7$ is H; F; $CF_3$; $C_{1-8}$-alkyl; $C_{2-8}$-alkenyl; $C_{2-8}$-alkynyl; cycloalkyl; heterocycloalkyl; $-(CHR^{12})_rOR^{15}$; $-O(CO)R^{15}$; $-(CHR^{12})_rSR^{15}$; $-(CHR^{10})_rNR^{15}R^{16}$; $-(CHR^{12})_rOCONR^{15}R^{16}$; $-(CHR^{12})_rNR^1CONR^{15}R^{16}$; $-(CHR^{12})_rNR^1COOR^{15}$; $-(CHR^{12})_rNR^1COR^{15}$; $-(CHR^{12})_oCOOR^{15}$; $-(CHR^{12})_oCONR^{15}R^{16}$; $-(CHR^{12})_rPO(OR^1)_2$; $-(CHR^{12})_rSO_2R^{15}$; $-(CHR^{12})_rNR^1SO_2R^{15}$; or $-(CHR^{12})_rSO_2NR^{15}R^{16}$;

$R^8$ and $R^9$ are, with the proviso of containing combined less than 26 carbon- and/or heteroatoms, independently $C_{1-8}$-alkyl; $C_{2-8}$-alkenyl; $C_{2-8}$-alkynyl; cycloalkyl-$C_{1-4}$-alkyl; heterocycloalkyl-$C_{1-4}$-alkyl; $-(CHR^1)_sOCF_3$; $-(CHR^1)_sOR^{18}$; $-(CHR^1)_sSCF_3$; or $-(CHR^1)_sSR^{18}$;

Z is selected from the group consisting of, with the proviso of containing less than 26 carbon- and/or heteroatoms,
  $-(CR^2R^{12})_q-$; $-(CR^2R^{12})_kO(CR^2R^{12})_l-$; $-(CR^2R^{12})_kS(CR^2R^{12})_l-$;

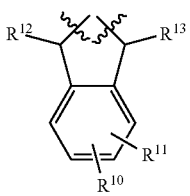
(Z1)

-continued

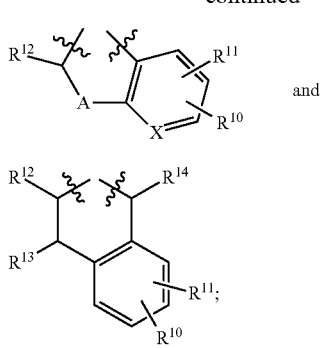

A is O; NR$^{17}$; S; SO; or SO$_2$;

X is —CR$^{19}$; or N;

R$^{10}$ and R$^{11}$ are independently
H; F; C$_1$; Br; I; CF$_3$; OCF$_3$; OCHF$_2$; C$_{1-4}$-alkyl; C$_{2-4}$-alkenyl; or C$_{2-4}$-alkynyl;

R$^{12}$, R$^{13}$ and R$^{14}$ are independently
H; F; CF$_3$; or CH$_3$;

R$^{15}$ and R$^{16}$ are independently
H; C$_{1-8}$-alkyl; C$_{2-8}$-alkenyl; C$_{2-8}$-alkynyl; C$_{1-6}$-alkoxy; cycloalkyl; heterocycloalkyl; cycloalkyl-C$_{1-6}$-alkyl; or heterocycloalkyl-C$_{1-6}$-alkyl; or the structural element —NR$^{15}$R$^{16}$ can form heterocycloalkyl;

R$^{17}$ is H; C$_{1-4}$-alkyl; C$_{2-4}$-alkenyl; or C$_{2-4}$-alkynyl;

R$^{18}$ is C$_{1-4}$-alkyl; C$_{2-4}$-alkenyl; or C$_{2-4}$-alkynyl;

R$^{19}$ is H; F; Cl; Br; I; CN; CF$_3$; OCHF$_2$; OCF$_3$; C$_{1-4}$-alkyl; C$_{2-4}$-alkenyl; or C$_{2-4}$ alkynyl;

R$^{20}$ and R$^{21}$ are independently
H; CF$_3$; C$_{1-8}$-alkyl; C$_{2-8}$-alkenyl; C$_{2-8}$-alkynyl; or aryl-C$_{1-6}$-alkyl;

R$^{22}$ is H; F; CF$_3$; C$_{1-8}$-alkyl; C$_{2-8}$-alkenyl; C$_{2-8}$-alkynyl; cycloalkyl; heterocycloalkyl; aryl; heteroaryl; aryl-C$_{1-6}$-alkyl; heteroaryl-C$_{1-6}$-alkyl; —(CHR$^{23}$)$_o$OR$^{25}$; —O(CO)R$^{25}$; —(CHR$^{23}$)$_o$SR$^{25}$; —(CHR$^{23}$)$_o$NR$^{25}$R$^{26}$; —(CHR$^{23}$)$_o$OCONR$^{25}$R$^{26}$; —(CHR$^{23}$)$_o$NR$^{20}$CONR$^{25}$R$^{26}$; —(CHR$^{23}$)$_o$NR$^{20}$COOR$^{25}$; —(CHR$^{23}$)$_o$NR$^{20}$COR$^{25}$; —(CHR$^{23}$)$_o$COOR$^{25}$; —(CHR$^{23}$)$_o$CONR$^{25}$R$^{26}$; —(CHR$^{23}$)$_o$PO(OR$^{20}$)$_2$; —(CHR$^{23}$)$_o$SO$_2$R$^{25}$; —(CHR$^{23}$)$_o$NR$^{20}$SO$_2$R$^{25}$; —(CHR$^{23}$)$_o$SO$_2$NR$^{25}$R$^{26}$; —(CR$^{20}$R$^{23}$)$_o$R$^{27}$; or —(CHR$^{20}$)$_n$O(CHR$^{21}$)$_m$R$^{27}$;

R$^{23}$ is H; F; CF$_3$; C$_{1-8}$-alkyl; C$_{2-8}$-alkenyl; C$_{2-8}$-alkynyl; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; —(CHR$^{20}$)$_o$OR$^{25}$; —OCOR$^{20}$; —(CHR$^{20}$)NR$^{25}$R$^{26}$; —COOR$^{25}$; —CONR$^{25}$R$^{26}$; —SO$_2$R$^{25}$; or -SO$_2$NR$^{25}$R$^{26}$;

R$^{24}$ is H; CF$_3$; C$_{1-8}$-alkyl; C$_{2-8}$-alkenyl; C$_{2-8}$-alkynyl; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; —(CHR$^{20}$)$_o$OR$^{25}$; —(CHR$^{20}$)$_o$SR$^{25}$; —(CHR$^{20}$)$_o$NR$^{25}$R$^{26}$; —(CHR$^{20}$)$_o$COOR$^{25}$; —(CHR$^{20}$)$_o$CONR$^{25}$R$^{26}$; or —(CHR$^{20}$)$_o$SO$_2$R$^{25}$;

R$^{25}$ and R$^{26}$ are independently
H; C$_{1-8}$-alkyl; C$_{2-8}$-alkenyl; C$_{2-8}$-alkynyl; C$_{1-6}$-alkoxy; cycloalkyl; heterocycloalkyl; cycloalkyl-C$_{1-6}$-alkyl; heterocycloalkyl-C$_{1-6}$-alkyl; aryl; heteroaryl; aryl-C$_{1-6}$-alkyl; heteroaryl-C$_{1-6}$-alkyl; cycloalkyl-aryl; heterocycloalkyl-aryl; cycloalkyl-heteroaryl; heterocycloalkyl-heteroaryl; aryl-cycloalkyl;

aryl-heterocycloalkyl; heteroaryl-cycloalkyl; or heteroaryl-heterocycloalkyl; or the structural element —NR$^{25}$R$^{26}$ can independently form:
heterocycloalkyl; aryl-heterocycloalkyl; or heteroaryl-heterocycloalkyl;

R$^{27}$ is an aryl group selected from the group consisting of

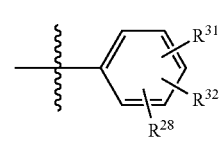

AR1

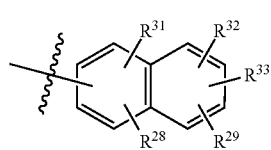

AR2

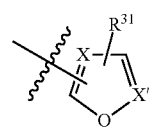

H1

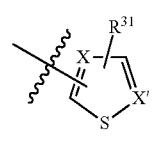

H2

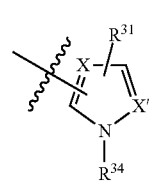

H3

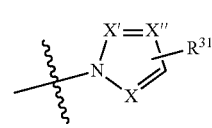

H4

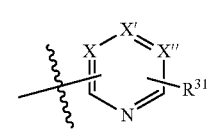

H5

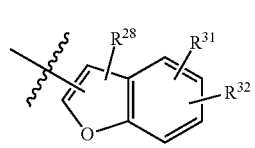

H6

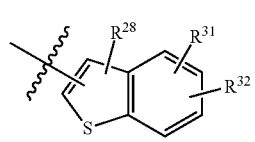

H7

-continued

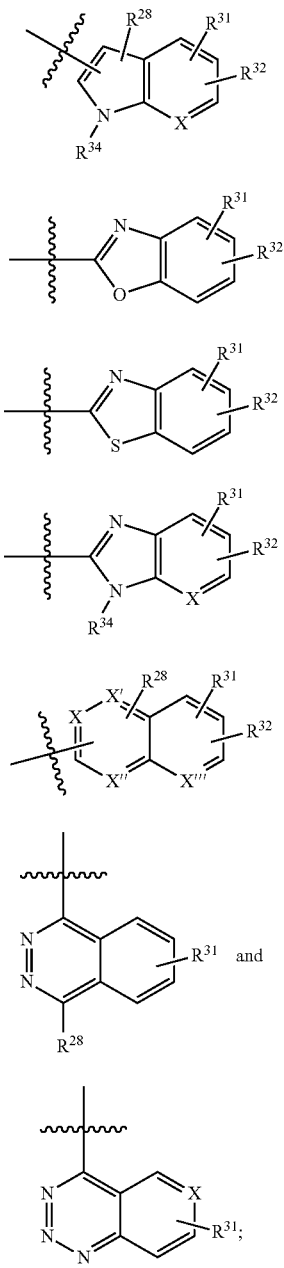

X, X', X" and X''' are independently
—CR²⁸; or N;

R²⁸ and R²⁹ are independently
H; F; Cl; Br; I; OH; NH₂; NO₂; CN; CF₃; OCHF₂; OCF₃; $C_{1-8}$-alkyl; $C_{2-8}$-alkenyl;
$C_{2-8}$-alkynyl; aryl; heteroaryl; aryl-$C_{1-6}$-alkyl; heteroaryl-$C_{1-6}$-alkyl; —(CH₂)ₒR³⁰;
—(CH₂)ₒOR²⁵; —O(CO)R²⁵;-O(CH₂)ₒR³⁰; —(CH₂)ₒSR²⁵; —(CH₂)ₒNR²⁵R²⁶;
—(CH₂)ₒOCONR²⁵R²⁶; —(CH₂)ₒNR²⁰CONR²⁵R²⁶; —(CH₂)ₒNR²⁰COR²⁵; —(CH₂)ₒCOOR²⁵;
—(CH₂)ₒCONR²⁵R²⁶; —(CH₂)ₒPO(OR²⁰)₂; —(CH₂)ₒSO₂R²⁴; or —(CH₂)ₒCOR²⁵;

R³⁰ is an aryl group of the formula

AR3

R³¹, R³² and R³³ are independently
H; F; Cl; Br; I; OH; NH₂; NO₂; CN; CF₃; OCHF₂; OCF₃; $C_{1-8}$-alkyl; $C_{2-8}$-alkenyl; $C_{2-8}$-alkynyl;
—(CH₂)ₒOR²⁵; —O(CO)R²⁵; —(CH₂)ₒNR²⁰R²⁵; —(CH₂)ₒCOOR²⁵; or
—(CH₂)ₒCONR²⁰R²⁵;

R³⁴ is H; Ac; $C_{1-8}$-alkyl; or aryl-$C_{1-6}$-alkyl;
k and l are independently an integer of 1-5 with the proviso that k+l≤6;
t and u are independently an integer of 0-3 with the proviso that t+u≥1 and t+u≤3;
n and m are independently an integer of 0-5 with the proviso that n+m≤6;
o is 0-4; p is 2-4; q is 3-7; r is 1-3; s is 1-4;
or a pharmaceutically acceptable salt thereof.

2. The compound according to claim 1 wherein
P¹ is Phe; Tyr; 3Pal; 2Thi; or 3Thi;
P² is Asp; Asn; Glu; Hgl; Gln; hGln; Cit; Bbta; 2Pal; 3Pal; 4Pal; h2Pal; h3Pal; h4Pal; Ala(2Furyl); Ala(3Furyl); Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); Ala(4Quin); Phe; Phe(4NH₂); Phe(mC(NH₂)=NH); Phe(pC(NH₂)=NH); Phe(2Cl); Phe(3Cl); Phe(4Cl); Phe(3,4C₁₂); Phe(2F); Phe(3F); Phe(4F); Phe(3CN); Phe(4CN); Phe(2CF₃); Phe(3CF₃); Phe(4CF₃); Phe(3,4(CF₃)2); Phe(4COOMe); hPhe; Phg; 1Nal; 2Nal; Nle(6OBn); Ser(Bn); Thr(Bn); Trp; Trp(7Aza); Trp(5Br); Trp(6Br); Trp(6CF₃); Trp(5Cl); Trp(6Cl); Trp(5,6Cl); Trp(5OH); hTrp; His; His(Me); His(Bn); hHis; 2Thi; 3Thi; Tyr; Tyr(3F); Tyr(Bn); Tyr(Me); Tyr(Ph); Tyr(4OHPh); hTyr; or Tza;
P³ is Leu; Nle; Cha; Chg; Asn; Gln; hGln; or Cit;
P⁴ is Leu; Nle; Val; Bbta; 2Pal; 3Pal; 4Pal; h2Pal; h3Pal; h4Pal; Ala(2Furyl); Ala(3Furyl); Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); Ala(4Quin); Phe; Phe(4NH₂); Phe(mC(NH₂)=NH); Phe(pC(NH₂)=NH); Phe(2Cl); Phe(3Cl); Phe(4Cl); Phe(3,4C₁₂); Phe(2F); Phe(3F); Phe(4F); Phe(3CN); Phe(4CN); Phe(2CF₃); Phe(3CF₃); Phe(4CF₃); Phe(3,4(CF₃)2); Phe(4COOMe); hPhe; Phg; 1Nal; 2Nal; Nle(6OBn); Ser(Bn); Thr(Bn); Trp; Trp(7Aza);
Trp(5Br); Trp(6Br); Trp(6CF₃); Trp(5Cl); Trp(6Cl); Trp(5,6Cl);Trp(5OH); hTrp; His; His(Me);
His(Bn); hHis; 2Thi; 3Thi; Tyr; Tyr(3F); Tyr(Bn); Tyr(Me); Tyr(Ph); Tyr(4OHPh); hTyr; or Tza;
P⁵ is Ala; Aib; or Abu;
P⁶ is Trp; Trp(5OH); Tpi; or Trp(1Me);
P⁷ is Asp; Asn; Glu; Hgl; Gln; hGln; or Cit;
P⁸ is Bbta; 2Pal; 3Pal; 4Pal; h2Pal; h3Pal; h4Pal; Ala (2Furyl); Ala(3Furyl); Ala(1Im); Ala(2Im);
hAla(1Im); hAla(2Im); Ala(Pyrazinyl); Ala(1Pyrazolyl); Ala(3Pyrazolyl); Ala(2Pyrimidin);
Ala(4Pyrimidin); Ala(5Pyrimidin); Ala(2Quin); Ala (3Quin); Ala(4Quin); Phe; Phe(4NH₂);
Phe(mC(NH₂)=NH); Phe(pC(NH₂)=NH); Phe(2Cl); Phe(3Cl); Phe(4Cl); Phe(3,4C₁₂); Phe(2F);

Phe(3F); Phe(4F); Phe(3CN); Phe(4CN); Phe(2CF$_3$); Phe(3CF$_3$); Phe(4CF$_3$); Phe(3,4(CF$_3$)2); Phe(4COOMe); hPhe; Phg; 1Nal; 2Nal; Nle(6OBn); Ser(Bn); Thr(Bn); Trp; Trp(7Aza);
Trp(5Br); Trp(6Br); Trp(6CF$_3$); Trp(5Cl); Trp(6Cl); Trp(5,6Cl); Trp(5OH); hTrp; His; His(Me);
His(Bn); hHis; 2Thi; 3Thi; Tyr; Tyr(3F); Tyr(Bn); Tyr(Me); Tyr(Ph); Tyr(4OHPh); hTyr; Tza;
Arg; hArg; Agp; Lys; hLys; or Orn;
with the proviso that
if P$^3$ is Asn; Gln; hGln; or Cit; then
    P$^2$ is Bbta; 2Pal; 3Pal; 4Pal; h2Pal; h3Pal; h4Pal; Ala(2Furyl); Ala(3Furyl); Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); Ala(4Quin); Phe; Phe(4NH$_2$); Phe(mC(NH$_2$)=NH); Phe(pC(NH$_2$)=NH); Phe(2Cl); Phe(3Cl); Phe(4Cl); Phe(3,4C$_{12}$); Phe(2F); Phe(3F); Phe(4F); Phe(3CN); Phe(4CN); Phe(2CF$_3$); Phe(3CF$_3$); Phe(4CF$_3$); Phe(3,4(CF$_3$)2); Phe(4COOMe); hPhe; Phg; 1Nal; 2Nal; Nle(6OBn); Ser(Bn); Thr(Bn); Trp; Trp(7Aza); Trp(5Br); Trp(6Br); Trp(6CF$_3$); Trp(5Cl); Trp(6Cl); Trp(5,6Cl); Trp(5OH); hTrp; His; His(Me); His(Bn); hHis; 2Thi; 3Thi; Tyr; Tyr(3F); Tyr(Bn); Tyr(Me); Tyr(Ph); Tyr(4OHPh); hTyr; or Tza;
    P$^7$ is Asp; Glu; Hgl; or Cit;
or if P$^3$ is Leu; Nle; Cha; or Chg; then
    P$^2$ is Asp; Asn; Glu; Hgl; Gln; hGln; Cit; Bbta; 2Pal; 3Pal; 4Pal; h2Pal; h3Pal; h4Pal; Ala(2Furyl); Ala(3Furyl); Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); Ala(4Quin); Phe; Phe(4NH$_2$); Phe(mC(NH$_2$)=NH); Phe(pC(NH$_2$)=NH); Phe(2Cl); Phe(3Cl); Phe(4Cl); Phe(3,4C$_{12}$); Phe(2F); Phe(3F); Phe(4F); Phe(3CN); Phe(4CN); Phe(2CF$_3$); Phe(3CF$_3$); Phe(4CF$_3$); Phe(3,4(CF$_3$)2); Phe(4COOMe); hPhe; Phg; 1Nal; 2Nal; Nle(6OBn); Ser(Bn); Thr(Bn); Trp; Trp(7Aza); Trp(5Br); Trp(6Br); Trp(6CF$_3$); Trp(5Cl); Trp(6Cl); Trp(5,6Cl); Trp(5OH); hTrp; His; His(Me); His(Bn); hHis; 2Thi; 3Thi; Tyr; Tyr(3F); Tyr(Bn); Tyr(Me); Tyr(Ph); Tyr(4OHPh); hTyr; or Tza;
    and with the further proviso that
    if P$^2$ is Asn; Gln; hGln; Cit; Bbta; 2Pal; 3Pal; 4Pal; h2Pal; h3Pal; h4Pal; Ala(2Furyl); Ala(3Furyl); Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); Ala(4Quin); Phe; Phe(4NH$_2$); Phe(mC(NH$_2$)=NH); Phe(pC(NH$_2$)=NH); Phe(2Cl); Phe(3Cl); Phe(4Cl); Phe(3,4C$_{12}$); Phe(2F); Phe(3F); Phe(4F); Phe(3CN); Phe(4CN); Phe(2CF$_3$); Phe(3CF$_3$); Phe(4CF$_3$); Phe(3,4(CF$_3$)2); Phe(4COOMe); hPhe; Phg; 1Nal; 2Nal; Nle(6OBn); Ser(Bn); Thr(Bn); Trp; Trp(7Aza); Trp(5Br); Trp(6Br); Trp(6CF$_3$); Trp(5Cl); Trp(6Cl); Trp(5,6Cl); Trp(5OH); hTrp; His; His(Me); His(Bn); hHis; 2Thi; 3Thi; Tyr; Tyr(3F); Tyr(Bn); Tyr(Me); Tyr(Ph); Tyr(4OHPh); hTyr; or Tza; then
        P$^7$ is Glu; or Hgl;
or a pharmaceutically acceptable salt thereof.

3. The compound according to claim 1 or 2 wherein
P$^1$ is Phe; 3Pal; 2Thi; or 3Thi;
P$^2$ is Glu; Hgl; Gln; or Cit; Phe; Phe(4NH$_2$); Phe(4F); Phe(4Cl); 3Pal; 4Pal; Tyr; Tyr(Me); Tyr(Ph); Tyr(Bn); His; His(Bn); Trp; or Trp(5OH);
P$^3$ is Leu; Nle; Cha; Chg; Gln; or Cit;
P$^4$ is Leu; Nle; Val; Phe; hPhe; Phe(4NH$_2$); Phe(4Cl); Phe(4CN); 4Pal; Tyr; Tyr(Me); Tyr(Ph); His; or 2Thi;
P$^5$ is Ala; Aib; or Abu;
P$^6$ is Trp; or Trp(1Me);
P$^7$ is Asp; Glu; Hgl; Gln; or Cit;
P$^8$ is Phe; Phg; hPhe; Phe(4NH$_2$); Phe(3Cl); Phe(4Cl); Phe(4CN); 3Pal; Tyr; Tyr(Me); Tyr(Bn); His; His(Bn); 2Thi; 3Thi; Trp; Trp(5OH); Arg; or Lys;
with the proviso that
if P$^3$ is Gln; or Cit; then
    P$^2$ is Phe; Phe(4NH$_2$); Phe(4F); Phe(4Cl); 3Pal; 4Pal; Tyr; Tyr(Me); Tyr(Ph);
    Tyr(Bn); His; His(Bn); Trp; or Trp(5OH);
    P$^7$ is Asp; Glu; Hgl; or Cit;
or if P$^3$ is Leu; Nle; Cha; or Chg; then
    P$^2$ is Glu; Hgl; Gln; Cit; His; or Trp;
    and with the further proviso that
    if P$^2$ is Gln; Cit; His; or Trp; then
        P$^7$ is Glu; or Hgl;
or a pharmaceutically acceptable salt thereof.

4. The compound according to claim 1, wherein
P$^1$ is Phe;
P$^2$ is Glu; Gln; Phe; Phe(4NH$_2$); 3Pal; 4Pal; Tyr; Tyr(Me); Tyr(Ph); Tyr(Bn); His; His(Bn); Trp; or Trp(5OH);
P$^3$ is Leu; or Gln;
P$^4$ is Leu; Phe; Phe(4CN); Tyr; or Tyr(Me);
P$^5$ is Ala;
P$^6$ is Trp;
P$^7$ is Glu; Hgl; Gln; or Cit;
P$^8$ is Phe; Phg; Phe(4NH$_2$); 3Pal; Tyr; Tyr(Me); Tyr(Bn); His; His(Bn); Trp; Trp(5OH); or Arg;
with the proviso that
if P$^3$ is Gln; then
    P$^2$ is Phe; Phe(4NH$_2$); 3Pal; 4Pal; Tyr; Tyr(Me); Tyr(Ph); Tyr(Bn); His; His(Bn); Trp or Trp(5OH);
    P$^7$ is Glu; Hgl; or Cit;
or if P$^3$ is Leu; then
    P$^2$ is Glu; Gln; His; or Trp;
    and with the further proviso that
    if P$^2$ is Gln; His; or Trp; then
        p$^7$ is Glu; or Hgl;
or a pharmaceutically acceptable salt thereof.

5. The compound according to claim 1, wherein
T$^1$ is $^D$Pro; $^D$Azt; $^D$Pro(5,5Me$_2$); $^D$Pro((4S)NH$_2$); $^D$Pro((4R)NH$_2$); $^D$Pro((3R)OH); $^D$Pro((3S)OH); $^D$Pro((4R)OH); or $^D$Pro((4S)OH);
T$^2$ is Aib; Deg; Dpg; Ac4c; 3,3-AC-OXT; Cyp; Chx; Chx(4oxo); 4,4-AC-THP; Ac7c; Ac8c; Atc; or Ind;
or pharmaceutically acceptable salts thereof.

6. The compound according to claim 1, wherein
T$^1$ is $^D$Pro; or $^D$Pro(5,5Me$_2$);
T$^2$ is Aib; Deg; Dpg; Ac4c; 3,3-AC-OXT; Cyp; Chx; 4,4-AC-THP; Ac7c; Ac8c; or Ind;
or a pharmaceutically acceptable salt thereof.

7. The compound according to claim 1, wherein
T$^1$ is $^D$Pro;
T$^2$ is Aib; Deg; Dpg; Cyp; Chx; Ac7c; Ac8c; or Ind;
or a pharmaceutically acceptable salt thereof.

8. The compound according to claim 1, which is
cyclo(-Phe-Phe-Gln-Tyr-Ala-Trp-Glu-Tyr-$^D$Pro-Chx-);
cyclo(-Phe-3Pal-Gln-Tyr-Ala-Trp-Glu-Tyr-$^D$Pro-Chx-);

cyclo(-Phe-Phe(4NH$_2$)-Gln-Tyr-Ala-Trp-Glu-Tyr-$^D$Pro-Chx-);
cyclo(-Phe-His(Bn)-Gln-Tyr-Ala-Trp-Glu-Tyr-$^D$Pro-Chx-);
cyclo(-Phe-Tyr(Bn)-Gln-Tyr-Ala-Trp-Glu-Tyr-$^D$Pro-Chx-);
cyclo(-Phe-Tyr(Ph)-Gln-Tyr-Ala-Trp-Glu-Arg-$^D$Pro-Chx-);
cyclo(-Phe-Tyr(Ph)-Gln-Tyr-Ala-Trp-Glu-Tyr-$^D$Pro-Chx-);
cyclo(-Phe-Trp-Gln-Tyr(Me)-Ala-Trp-Glu-Tyr-$^D$Pro-Chx-);
cyclo(-Phe-Trp-Gln-Tyr-Ala-Trp-Glu-Tyr(Me)-Pro-Chx-);
cyclo(-Phe-Phe-Gln-Tyr-Ala-Trp-Glu-Arg-Pro-Chx-);
cyclo(-Phe-Tyr(Ph)-Gln-Tyr-Ala-Trp-Glu-Arg-$^D$Pro-Aib-);
cyclo(-Phe-Trp-Leu-Tyr-Ala-Trp-Glu-Tyr-$^D$Pro-Chx-);
cyclo(-Phe-Glu-Leu-Tyr-Ala-Trp-Glu-Tyr-$^D$Pro-Ind-);
cyclo(-Phe-Tyr-Gln-Tyr-Ala-Trp-Glu-Tyr-$^D$Pro-Chx-);
cyclo(-Phe-Trp-Gln-Tyr-Ala-Trp-Glu-His(Bn)-$^D$Pro-Chx-);
cyclo(-Phe-Glu-Leu-Tyr-Ala-Trp-Glu-Trp-$^D$Pro-Chx-);
cyclo(-Phe-Trp-Gln-Tyr-Ala-Trp-Glu-Trp-$^D$Pro-Chx-);
cyclo(-Phe-Trp-Gln-Tyr-Ala-Trp-Glu-Trp(5 OH)$^D$Pro-Chx-);
cyclo(-Phe-3Pal-Gln-Tyr-Ala-Trp-Glu-Arg-$^D$Pro-Chx-);
cyclo(-Phe-His-Leu-Tyr-Ala-Trp-Glu-Tyr-$^D$Pro-Chx-);
cyclo(-Phe-Phe(4NH$_2$)-Gln-Tyr-Ala-Trp-Glu-Arg-Pro-Chx-);
cyclo(-Phe-Trp-Gln-Tyr-Ala-Trp-Glu-Tyr(Bn)-Pro-Chx-);
cyclo(-Phe-Trp-Gln-Tyr(Me)-Ala-Trp-Glu-Arg-Pro-Chx-);
cyclo(-Phe-Trp-Gln-Tyr-Ala-Trp-Glu-Phe-$^D$Pro-Chx-);
cyclo(-Phe-Glu-Leu-Tyr-Ala-Trp-Glu-Trp(5OH)-$^D$Pro-Chx-);
cyclo(-Phe-Glu-Leu-Leu-Ala-Trp-Glu-Phe-$^D$Pro-Dpg-);
cyclo(-Phe-Trp-Gln-Phe-Ala-Trp-Glu-Tyr-$^D$Pro-Chx-);
cyclo(-Phe-Glu-Leu-Tyr-Ala-Trp-Trp(5OH)-Tyr-$^D$Pro-Chx-);
cyclo(-Phe-Glu-Leu-Tyr(Me)-Ala-Trp-Glu-Tyr-$^D$Pro-Chx-);
cyclo(-Phe-Trp-Gln-Tyr-Ala-Trp-Glu-Phe(4NH$_2$)-$^D$Pro-Chx-);
cyclo(-Phe-Glu-Leu-Tyr-Ala-Trp-Glu-Phe-$^D$Pro-Chx-);
cyclo(-Phe-Tyr(Me)-Gln-Tyr-Ala-Trp-Glu-Tyr-$^D$Pro-Chx-);
cyclo(-Phe-4Pal-Gln-Tyr-Ala-Trp-Glu-Tyr-$^D$Pro-Chx-);
cyclo(-Phe-Glu-Leu-Tyr(Me)-Ala-Trp-Glu-Tyr(Me)-$^D$Pro-Chx-);
cyclo(-Phe-Trp(5OH)-Gln-Tyr-Ala-Trp-Glu-Tyr-$^D$Pro-Chx-);
cyclo(-Phe-Glu-Leu-Tyr-Ala-Trp-Glu-His(Bn)-$^D$Pro-Chx-);
cyclo(-Phe-Glu-Leu-Phe(4CN)-Ala-Trp-Glu-Tyr-$^D$Pro-Chx-);
cyclo(-Phe-Glu-Leu-Tyr-Ala-Trp-Cit-Tyr-$^D$Pro-Chx-);
cyclo(-Phe-Glu-Leu-Tyr-Ala-Trp-Glu-His-$^D$Pro-Chx-);
cyclo(-Phe-Gln-Leu-Tyr-Ala-Trp-Glu-Tyr-$^D$Pro-Chx-);
cyclo(-Phe-Glu-Leu-Tyr-Ala-Trp-Glu-3Pal-$^D$Pro-Chx-);
cyclo(-Phe-Glu-Leu-Tyr-Ala-Trp-Glu-Arg-$^D$Pro-Chx-);
cyclo(-Phe-Glu-Leu-Leu-Ala-Trp-Glu-Phe-$^D$Pro-Chx-);
cyclo(-Phe-Glu-Leu-Leu-Ala-Trp-Glu-Phe-$^D$Pro-Cyp-);
cyclo(-Phe-Glu-Leu-Leu-Ala-Trp-Glu-Phe-$^D$Pro-Aib-);
cyclo(-Phe-Trp-Gln-Leu-Ala-Trp-Glu-Phe-$^D$Pro-Cyp-);
cyclo(-Phe-Glu-Leu-Leu-Ala-Trp-Glu-Phe-$^D$Pro-Deg-);
cyclo(-Phe-Glu-Leu-Tyr-Ala-Trp-Glu-Phe-$^D$Pro-Cyp-);
cyclo(-Phe-Gln-Leu-Tyr-Ala-Trp-Glu-Hgl-Tyr-$^D$Pro-Chx-);
cyclo(-Phe-Glu-Leu-Tyr-Ala-Trp-Glu-Phg-$^D$Pro-Chx-);
cyclo(-Phe-His-Leu-Tyr-Ala-Trp-Gln-Tyr-$^D$Pro-Aib-);
cyclo(-Phe-Glu-Leu-Leu-Ala-Trp-Glu-Phe-$^D$Pro-Ind-);
cyclo(-Phe-Glu-Leu-Leu-Ala-Trp-Glu-Phe-$^D$Pro-Ac7c-);
cyclo(-Phe-Glu-Leu-Leu-Ala-Trp-Glu-Phe-$^D$Pro-Ac8c-);
or a pharmaceutically acceptable salt thereof.

9. The compound according to claim 8 which is cyclo(-Phe-Phe-Gln-Tyr-Ala-Trp-Glu-Tyr-$^D$Pro-Chx-);
cyclo(-Phe-3Pal-Gln-Tyr-Ala-Trp-Glu-Tyr-$^D$Pro-Chx-);
cyclo(-Phe-Phe(4NH$_2$)-Gln-Tyr-Ala-Trp-Glu-Tyr-$^D$Pro-Chx-);
cyclo(-Phe-His(Bn)-Gln-Tyr-Ala-Trp-Glu-Tyr-$^D$Pro-Chx-);
cyclo(-Phe-Tyr(Bn)-Gln-Tyr-Ala-Trp-Glu-Tyr-$^D$Pro-Chx-);
cyclo(-Phe-Tyr(Ph)-Gln-Tyr-Ala-Trp-Glu-Arg-$^D$Pro-Chx-);
cyclo(-Phe-Tyr(Ph)-Gln-Tyr-Ala-Trp-Glu-Tyr-$^D$Pro-Chx-);
cyclo(-Phe-Trp-Gln-Tyr(Me)-Ala-Trp-Glu-Tyr-$^D$Pro-Chx-);
cyclo(-Phe-Trp-Gln-Tyr-Ala-Trp-Glu-Tyr(Me)-$^D$Pro-Chx-);
cyclo(-Phe-Phe-Gln-Tyr-Ala-Trp-Glu-Arg-$^D$Pro-Chx-);
cyclo(-Phe-Tyr(Ph)-Gln-Tyr-Ala-Trp-Glu-Arg-$^D$Pro-Aib-);
cyclo(-Phe-Trp-Leu-Tyr-Ala-Trp-Glu-Tyr-$^D$Pro-Chx-);
cyclo(-Phe-Glu-Leu-Tyr-Ala-Trp-Glu-Tyr-$^D$Pro-Ind-);
cyclo(-Phe-Tyr-Gln-Tyr-Ala-Trp-Glu-Tyr-$^D$Pro-Chx-);
cyclo(-Phe-Trp-Gln-Tyr-Ala-Trp-Glu-His(Bn)-$^D$Pro-Chx-);
cyclo(-Phe-Glu-Leu-Tyr-Ala-Trp-Glu-Trp-$^D$Pro-Chx-);
cyclo(-Phe-Trp-Gln-Tyr-Ala-Trp-Glu-Trp-$^D$Pro-Chx-);
cyclo(-Phe-Trp-Gln-Tyr-Ala-Trp-Glu-Trp(5OH)-$^D$Pro-Chx-);
cyclo(-Phe-3Pal-Gln-Tyr-Ala-Trp-Glu-Arg-$^D$Pro-Chx-);
cyclo(-Phe-His-Leu-Tyr-Ala-Trp-Glu-Tyr-$^D$Pro-Chx-);
cyclo(-Phe-Phe(4NH$_2$)-Gln-Tyr-Ala-Trp-Glu-Arg-$^D$Pro-Chx-);
cyclo(-Phe-Trp-Gln-Tyr-Ala-Trp-Glu-Tyr(Bn)-$^D$Pro-Chx-);
cyclo(-Phe-Trp-Gln-Tyr(Me)-Ala-Trp-Glu-Arg-$^D$Pro-Chx-);
cyclo(-Phe-Trp-Gln-Tyr-Ala-Trp-Glu-Phe-$^D$Pro-Chx-);
cyclo(-Phe-Glu-Leu-Tyr-Ala-Trp-Glu-Trp(5OH)-$^D$Pro-Chx-);
cyclo(-Phe-Trp-Gln-Phe-Ala-Trp-Glu-Tyr-$^D$Pro-Chx-);
cyclo(-Phe-Glu-Leu-Tyr(Me)-Ala-Trp-Glu-Tyr-$^D$Pro-Chx-);
cyclo(-Phe-Trp-Gln-Tyr-Ala-Trp-Glu-Phe(4NH$_2$)-$^D$Pro-Chx-);
cyclo(-Phe-Glu-Leu-Tyr-Ala-Trp-Glu-Phe-$^D$Pro-Chx-);
cyclo(-Phe-Tyr(Me)-Gln-Tyr-Ala-Trp-Glu-Tyr-$^D$Pro-Chx-);
cyclo(-Phe-4Pal-Gln-Tyr-Ala-Trp-Glu-Tyr-$^D$Pro-Chx-);
cyclo(-Phe-Glu-Leu-Tyr(Me)-Ala-Trp-Glu-Tyr(Me)-$^D$Pro-Chx-);
cyclo(-Phe-Glu-Leu-Tyr-Ala-Trp-Glu-His(Bn)-$^D$Pro-Chx-);
cyclo(-Phe-Glu-Leu-Phe(4CN)-Ala-Trp-Glu-Tyr-$^D$Pro-Chx-);
cyclo(-Phe-Glu-Leu-Tyr-Ala-Trp-Cit-Tyr-$^D$Pro-Chx-);
cyclo(-Phe-Glu-Leu-Tyr-Ala-Trp-Glu-3Pal-$^D$Pro-Chx-);
cyclo(-Phe-Glu-Leu-Tyr-Ala-Trp-Glu-Phe-$^D$Pro-Cyp-);
cyclo(-Phe-Glu-Leu-Leu-Ala-Trp-Glu-Phe-$^D$Pro-Ind-);
or a pharmaceutically acceptable salt thereof.

10. The compound according to claim 8 which is
cyclo(-Phe-Phe-Gln-Tyr-Ala-Trp-Glu-Tyr-$^D$Pro-Chx-);
cyclo(-Phe-His(Bn)-Gln-Tyr-Ala-Trp-Glu-Tyr-$^D$Pro-Chx-);
cyclo(-Phe-Phe(4NH$_2$)-Gln-Tyr-Ala-Trp-Glu-Tyr-$^D$Pro-Chx-);
cyclo(-Phe-Tyr(Bn)-Gln-Tyr-Ala-Trp-Glu-Tyr-$^D$Pro-Chx-);
cyclo(-Phe-Tyr(Ph)-Gln-Tyr-Ala-Trp-Glu-Arg-Pro-Chx-);
cyclo(-Phe-3Pal-Gln-Tyr-Ala-Trp-Glu-Tyr-$^D$Pro-Chx-);
cyclo(-Phe-Trp-Gln-Tyr(Me)-Ala-Trp-Glu-Tyr-$^D$Pro-Chx-);
cyclo(-Phe-Phe-Gln-Tyr-Ala-Trp-Glu-Arg-Pro-Chx-);
or a pharmaceutically acceptable salt thereof.

11. The compound according to claim 1, having modulating activity at the GLP-1 receptor.

12. The compound of formula (I) according to claim 1, or a pharmaceutically acceptable salt thereof, for use as a medicament.

13. A pharmaceutical composition containing a compound or a mixture of compounds according to claim 1, and at least one pharmaceutically inert carrier.

14. The pharmaceutical composition according to claim 13 in a form suitable for oral, topical, transdermal, injection, buccal, transmucosal, rectal, pulmonary or inhalation administration, especially in the form of tablets, dragees, capsules, solutions, liquids, gels, plaster, creams, ointments, syrup, slurries, suspensions, depot preparations, spray, nebulizer or suppositories.

15. A process for the preparation of a compound according to claim 1, which comprises
    (a) coupling an appropriately functionalized solid support with an appropriately N-protected derivative of that amino acid which in the desired end-product is in position $T^1$ or $T^2$ or $P^1$ to $P^8$ as defined in claim 1; any functional group which may be present in said N-protected amino acid derivative being likewise appropriately protected;
    (b) removing the N-protecting group from the product obtained in step (a);
    (c) coupling the product thus obtained with an appropriately N-protected derivative of that amino acid which in the desired end-product is in the position of the next element (T or P), following counterclockwise or clockwise the sequence according to general formula (I) in —COOH to —NH$_2$ orientation; any functional group which may be present in said N-protected amino acid derivative being likewise appropriately protected;
    (d) removing the N-protecting group from the product thus obtained;
    (e) repeating steps (c) and (d) until all amino acid residues have been introduced;
    (f) detaching the product thus obtained from the solid support;
    (g) cyclizing the product cleaved from the solid support;
    (h) removing any protecting groups present on functional groups of any members of the chain of amino acid residues and, if desired, any protecting group(s) which may in addition be present in the molecule;
    (i) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

* * * * *